US011479914B2

(12) United States Patent
Zhu et al.

(10) Patent No.: US 11,479,914 B2
(45) Date of Patent: Oct. 25, 2022

(54) FRACTIONATION OF LIGNOCELLULOSIC BIOMASS USING MALEIC ACID AT LOW TEMPERATURE

(71) Applicant: The United States as Represented by the Secretary of Agriculture, Washington, DC (US)

(72) Inventors: Junyong Zhu, Madison, WI (US); Roland Gleisner, Jefferson, WI (US)

(*) Notice: Subject to any disclaimer, the term of this patent is extended or adjusted under 35 U.S.C. 154(b) by 130 days.

(21) Appl. No.: 16/990,459

(22) Filed: Aug. 11, 2020

(65) Prior Publication Data
US 2022/0049419 A1 Feb. 17, 2022
US 2022/0290369 A9 Sep. 15, 2022

Related U.S. Application Data

(60) Provisional application No. 62/885,393, filed on Aug. 12, 2019.

(51) Int. Cl.
*D21C 3/04* (2006.01)
*D21C 9/08* (2006.01)
*C12P 19/14* (2006.01)
*C12P 19/02* (2006.01)

(52) U.S. Cl.
CPC ............... *D21C 3/04* (2013.01); *C12P 19/02* (2013.01); *C12P 19/14* (2013.01); *D21C 9/08* (2013.01)

(58) Field of Classification Search
CPC ... D21C 3/04; D21C 9/08; C12P 19/02; C12P 19/14
See application file for complete search history.

(56) References Cited

U.S. PATENT DOCUMENTS

| 8,835,141 | B2 | 9/2014 | Zhu | |
| 9,187,865 | B2 | 11/2015 | Nelson | |
| 9,447,539 | B2 | 9/2016 | Zhang | |
| 9,512,454 | B2 | 12/2016 | Jonsson | |
| 10,006,166 | B2* | 6/2018 | Zhu | .............. D21B 1/021 |
| 10,239,905 | B2* | 3/2019 | Zhu | .................. C07G 1/00 |
| 2016/0168363 | A1 | 6/2016 | Nelson | |

FOREIGN PATENT DOCUMENTS

AU 2016213871 B2 9/2016

OTHER PUBLICATIONS

Bian et al., Recyclable and Reusable Maleic Acid for Efficient Production of Cellulose Nanofibrils with Stable Performance. ACS Sustainable Chem. Eng., 2019, vol. 7: 20022-20031. (Year: 2019).*
Cai et al., Maleic acid as a dicarboxylic acid hydrotrope for sustainable fractionation of wood at atmospheric pressure and ≤100° C.: mode and utility of lignin esterification. Green Chem., 2020, vol. 22: 1605-1617. (Year: 2020).*
Cai et al., Comparison of Two Acid Hydrotropes for Sustainable Fractionation of Birch Wood. ChemSusChem., 2020, vol. 13: 4649-4659. (Year: 2020).*
Bian et al., Effect of fiber drying on properties of lignin containing cellulose nanocrystals and nanofibrils produced through maleic acid hydrolysis. Cellulose, 2017, vol. 24: 4205-4216. (Year: 2017).*
Bian et al., Producing wood-based nanomaterials by rapid fractionation of wood at 80° C. using a recyclable acid hydrotrope†. Green Chem., 2017, vol. 19: 3370-3379. (Year: 2017).*

* cited by examiner

*Primary Examiner* — Ganapathirama Raghu

(57) ABSTRACT

Methods of fractionating lignocellulosic biomass using maleic acids are provided. Also provided are methods of forming lignin particles, furans, sugars, and/or lignocellulosic micro- and nanofibrils from the liquid and solid fractions produced by fractionation process. The fractionation can be carried out at low temperatures with short reaction times to carboxylate and dissolve lignin with a low degree of condensation.

20 Claims, 21 Drawing Sheets

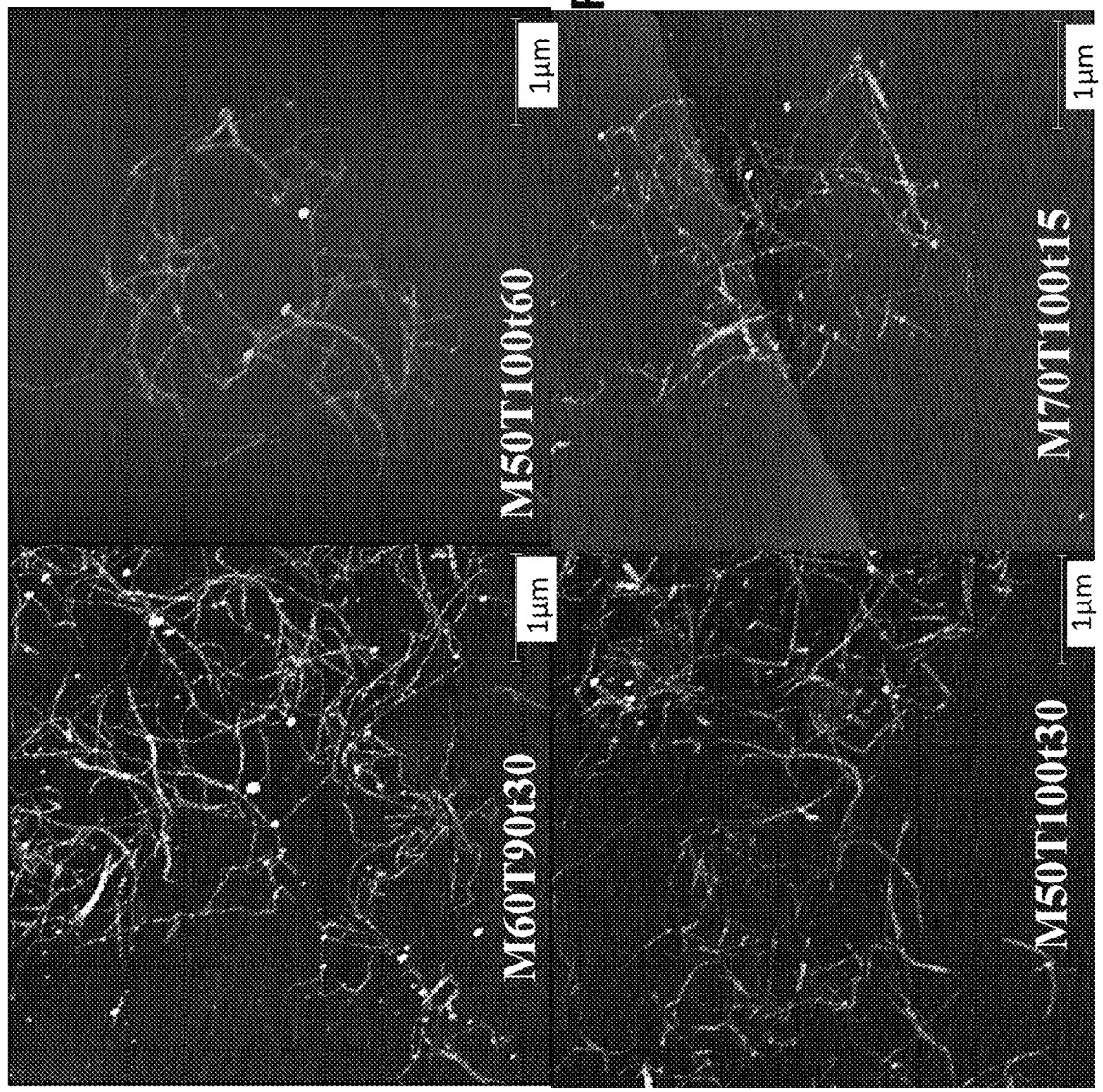

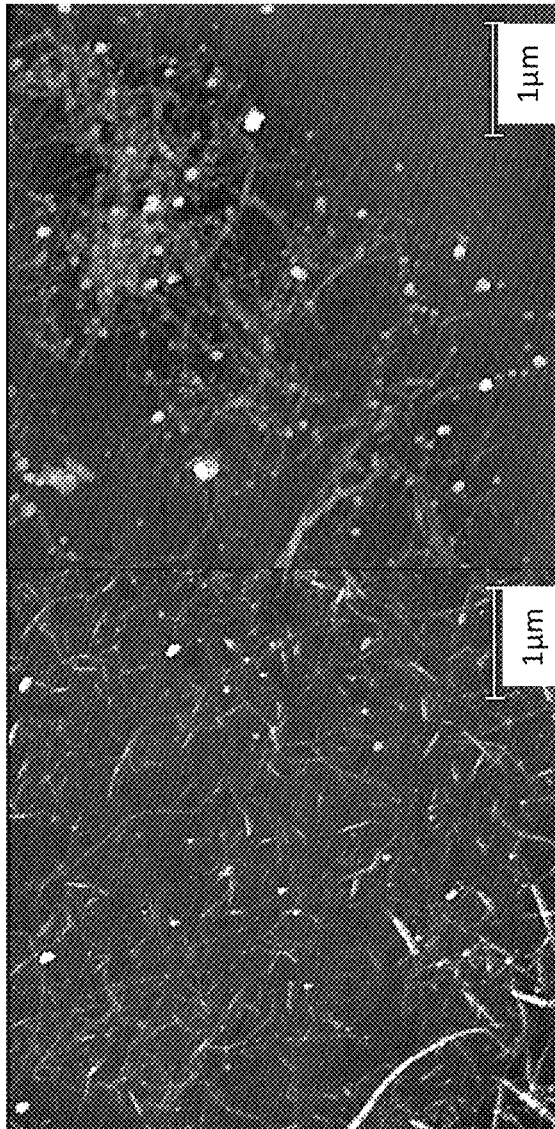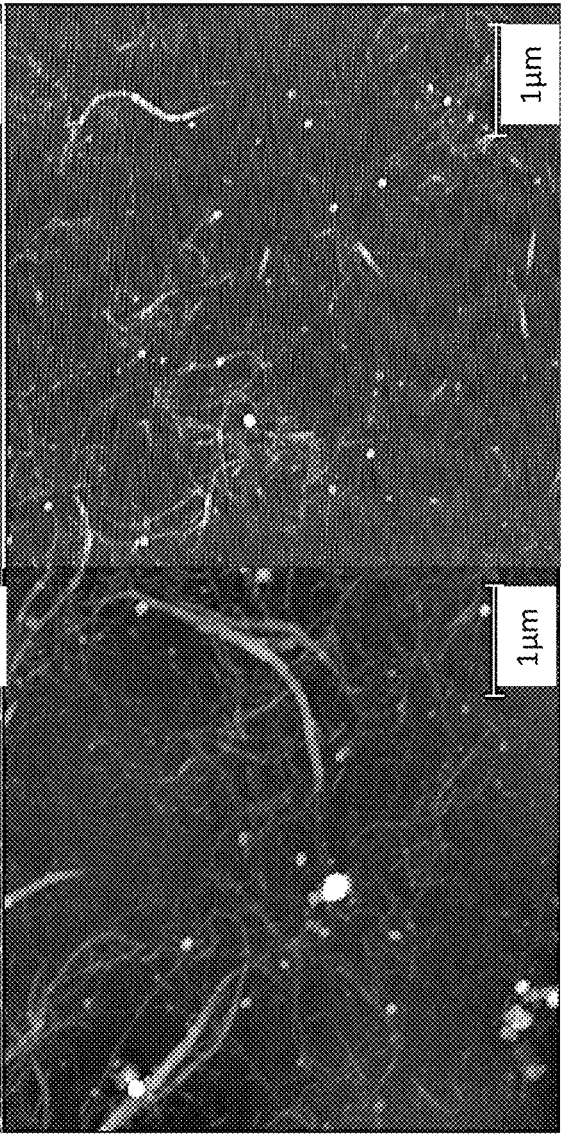
FIG. 10A (1 Pass)
FIG. 10B (3 passes)
FIG. 10C (1 pass)
FIG. 10D (3 passes)

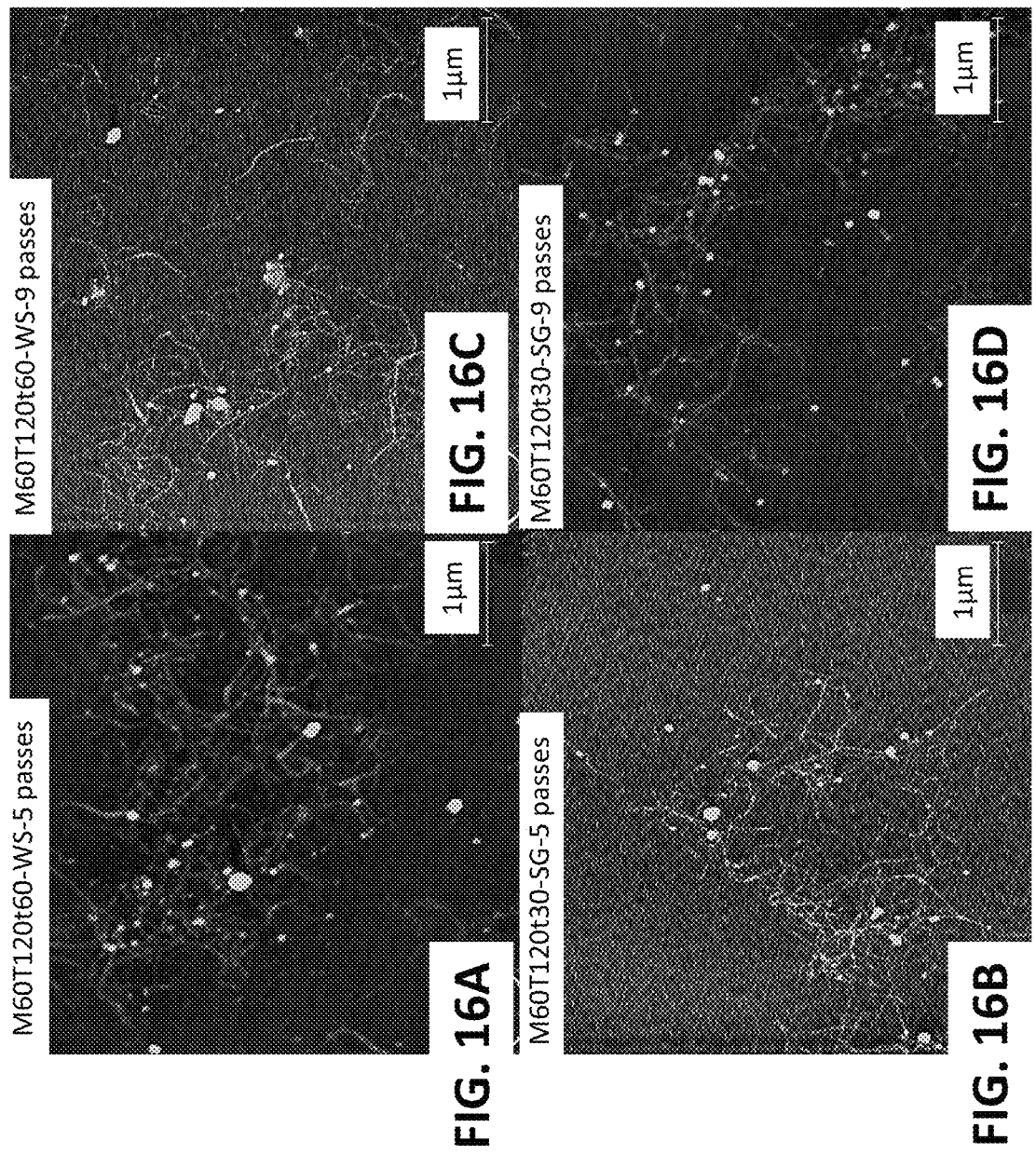

FRACTIONATION OF LIGNOCELLULOSIC BIOMASS USING MALEIC ACID AT LOW TEMPERATURE

CROSS-REFERENCE TO RELATED APPLICATIONS

The present application claims priority to U.S. provisional patent application No. 62/885,393 that was filed Aug. 12, 2019, the entire contents of which are incorporated herein by reference.

FIELD OF THE INVENTIONS

The inventions described herein relate to the field of fractionation of lignocellulosic plant biomass, such as woody biomass, for value added utilizations.

BACKGROUND

Advanced utilization of lignocellulosic biomass for producing chemicals, biofuels, and biomaterials requires efficient fractionation of lignocelluloses into usable building blocks. Effective and selective fractionation at atmospheric pressure and low temperatures with easy recovery of process chemicals is critically important to economical and sustainable utilization of lignocellulosic biomass through the biorefinery concept. The pulp and paper industry is the classical example of commercial implementation of fractionation technologies, i.e., alkaline or sulfite pulping for producing papermaking or dissolving pulp fibers using the carbohydrate fraction of lignocelluloses. While both alkaline and sulfite wood pulping are highly selective in dissolving wood lignin over carbohydrates, the dissolved wood lignin from both technologies, however, is highly condensed (Gellerstedt & Lindfors, 1984; Kringstad & Mörck, 1983; Rinaldi et al., 2016; Shuai et al., 2016) due to the use of harsh chemicals such as sulfite or sodium hydroxide and sodium sulfide and reaction conditions such as high temperatures of 125-170° C. for a period of 2 h or more. As a result, the commercial technical lignin from wood pulping is very difficult to be valorized through further conversion, excepting lignosulfonate from acidic sulfite pulping which can be directly marketed as a dispersant. Lignin from alkaline wood pulping is often used as a boiler fuel, a low-value utilization through combustion but a necessary common practice to achieve pulping chemical recovery and mill energy self-sufficiency.

Lignin valorization other than boiler fuel is necessary for the future of biorefinery operations. Fractionating lignin with low degree of condensation, i.e., high β-O-4 aryl-ether linkage contents, can facilitate further processing of lignin into biochemicals and biofuels (Sun et al., 2018). Unfortunately, existing fractionation technologies need elevated temperatures (Ewanick et al., 2007; Gu et al., 2016; Iakovlev & van Heiningen, 2012; Pan et al., 2006; Zhu et al., 2009). These conditions also result in condensed lignin that is difficult to be valorized (Deuss et al., 2017; Renders et al., 2017; Rinaldi et al., 2016). Use of a chemical stabilizer is capable of inhibiting lignin condensation (Shuai et al., 2016); however, the chemical stabilizers used are impractical on a large scale and introduce environmental concerns, even for broad research applications.

Demand for dissolving pulp fibers (DPF) is increasing due to population growth and shrinking cotton growing land. DPF is a necessary alternative to make up the large market shortage for cotton fibers. Dissolving pulp fibers are commercially produced at high temperatures for several hours, using either sulfite pulping or hot-water pre-hydrolysis coupled with kraft pulping, resulting in condensed lignin. Pulp bleaching is a necessary step to further remove lignin after commercial pulping to produce DPF. While commercial bleaching processes are effective, lignin condensation resulting from commercial pulping negatively impacts pulping bleaching and increases demand for bleaching chemicals. Recently, more attention has been paid to using herbaceous lignocelluloses or agricultural biomass for fiber production, partly due to environmental concerns for disposal. Atmospheric pressure delignification at low temperatures with a low degree of lignin condensation is very attractive for on-farm applications to address issues related to transportation of low-density biomass as well as reduced chemical application in bleaching. It is therefore desirable to develop novel fractionation/delignification technologies which do not condense lignin remaining on the pulp fibers.

Cellulose nanomaterials have attracted great interest recently for their unique optical and mechanical properties (Moon et al., 2011; Zhu et al., 2016). Lignin-containing cellulose nanomaterials (LCNMs) with increased thermostability and reduced hydrophilicity can be produced from commercial unbleached chemical pulps (Bian et al., 2017a; Rojo et al., 2015; Spence et al., 2010) or by using organosolv pulping (concentrated ethanol and sulfur dioxide) at high temperatures (Nelson et al., 2015). However, producing LCNMs directly from raw lignocelluloses using effective delignification at atmospheric pressure and low temperatures is much more desirable.

Long chain dicarboxylic acids, such as the commercial product DIACID C21, 5-carboxy-4-hexyl-2-cyclohexene-1-yl octanoic acid, have long been recognized with hydrotropic properties (Friberg et al., 1986; Mino et al., 1977; Ward et al., 1975). However, the feasibility of using this type of dicarboxylic acid for delignification was never attempted nor demonstrated, partially due to the conventional understanding that acidic conditions condense lignin and degrade carbohydrates to negatively impact fiber production. Furthermore, the low solubility at low temperature of these dicarboxylic acids may prevent their applications at low temperatures.

Concentrated solid dicarboxylic acids, such as oxalic acid and maleic acid, have been used to hydrolyze fully bleached wood fibers for producing lignin free cellulosic nanomaterials, i.e., cellulose nanocrystals (CNCs) and cellulose nanofibrils (CNFs) (Chen et al., 2016). In addition, concentrated maleic acid hydrolysis has been applied to commercial unbleached chemical pulps with lignin content up to 17.1% at acid concentration of 60 wt. % and 120° C. for 120 min (Bian et al., 2017a; Bian et al., 2017c). It was found that the maximum lignin removal was only 2.5% of the starting lignin in the unbleached pulp fibers (Bian et al., 2017a), which is within the margin of measurement errors and therefore negligible. These results suggest that maleic acid solutions cannot solubilize lignin.

SUMMARY

Methods of fractionating lignocellulosic biomass and, optionally, further downstream processing of the resulting lignin and solid residues are provided.

One embodiment of a method for fractionating lignocellulosic biomass includes the steps of: dispersing a lignocellulosic biomass in an aqueous solution comprising maleic acid, wherein the concentration of the maleic acid in the solution is higher than its minimal hydrotrope concentration;

reacting the lignocellulosic biomass with the maleic acid at a temperature and for a time sufficient to carboxylate the lignin and to dissolve at least 10 wt. % of the lignin in the lignocellulosic biomass; and separating the solution and the dispersed lignocellulosic biomass into a spent acid solution comprising dissolved carboxylated lignin and a water-insoluble cellulose-rich solids fraction. The methods are able to produce minimally condensed and carboxylated lignin, as well as cellulose.

Optionally, the spent acid solution can be further processed by precipitating out the dissolved lignin and/or by converting dissolved sugars into furans. Lignin-containing cellulose nanocrystals also may be separated from the resulting solution. The lignocellulosic solid residues, with or without separating the lignin-containing cellulose nanocrystals, can be further processed into fibers, with or without subsequent bleaching, via mechanical fibrillation, and/or converted into sugars via hydrolysis. The fibers include lignocellulosic microfibrils, lignocellulosic nanofibrils, or a combination thereof.

BRIEF DESCRIPTION OF THE DRAWINGS

Illustrative embodiments of the invention will hereafter be described with reference to the accompanying drawings, wherein like numerals denote like elements.

FIG. 4A: fractionation time; FIG. 4B: acid concentration; FIG. 4C: fractionation temperature.

FIGS. 6A-6D Maleic acid hydrotropic fractionation conditions (FIGS. 6A-6D) on resultant morphology of lignin containing cellulose nanofibrils (LCNFs) from birch wood observed by AFM.

FIGS. 10A-10F. Comparisons of LCNF morphology (FIGS. 10A-10D) and height distribution probability density (FIGS. 10E-10F) among LCFs derived from relatively severe fractionation conditions M60T110t30 (FIGS. 10A-10B) and M60T120t30 (FIGS. 10C-10D) with 1 pass (FIG. 10A and FIG. 10C) and 3 passes (FIG. 10B and FIG. 10D) microfluidization.

FIGS. 16A-16D. Maleic acid hydrotropic fractionation conditions (FIGS. 16A-16D) on resultant morphology of wheat straw (FIG. 16A and 16C) and switchgrass (FIG. 16B and 16D) lignin-containing cellulose nanofibrils (LCNFs) observed by AFM.

DETAILED DESCRIPTION

Figure 1:
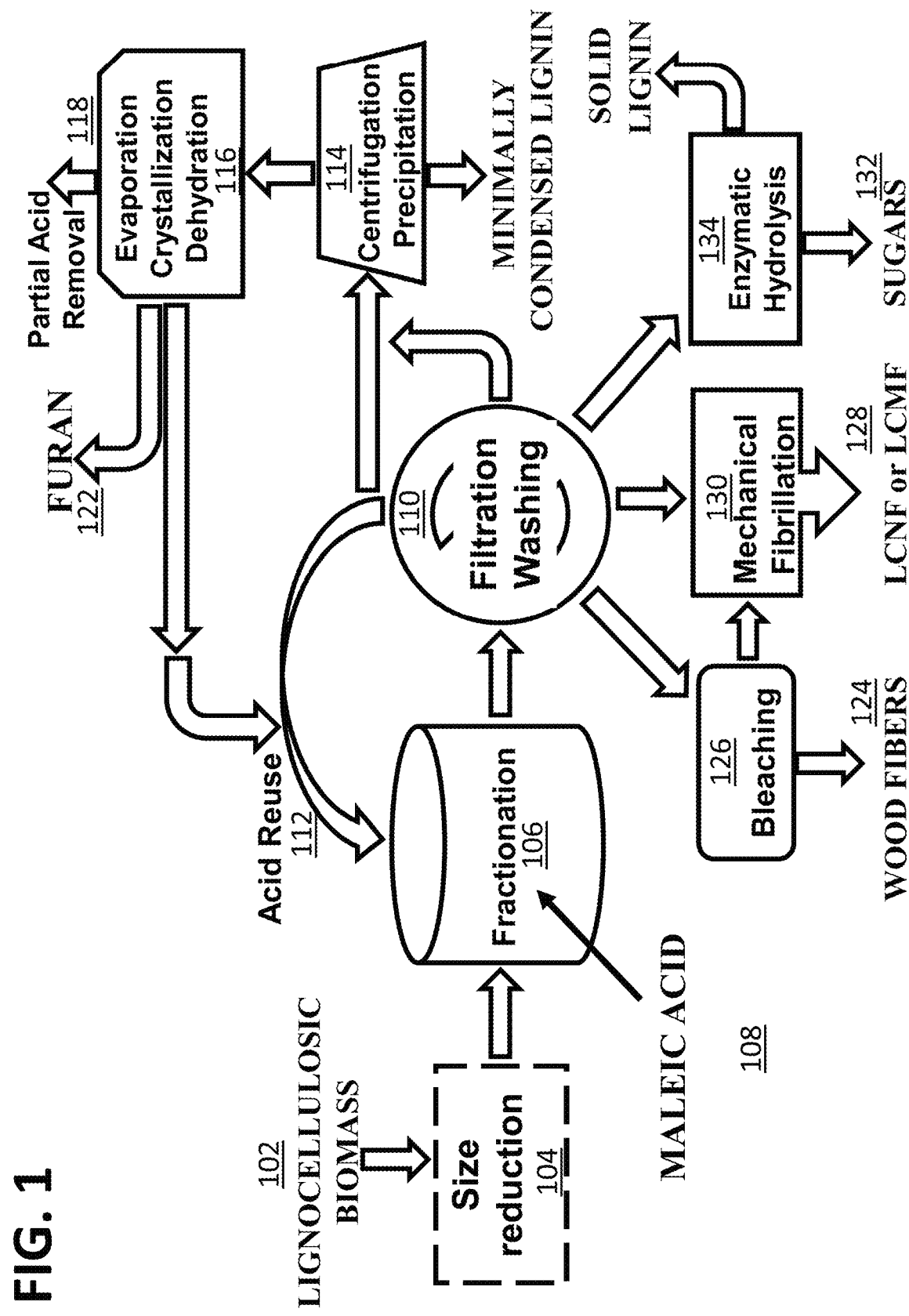
FIG. 1. One embodiment of the schematic flow diagram of the present invention for fractionation of lignocelluloses using maleic acid for producing fibers, lignocellulosic nanofibrils, sugars/biofuel, furans/Furfural, and acid recovery. Fractionation can also be conducted using continuous flow-through configuration as practiced in industry rather than batch mode.

Methods of fractionating lignocellulosic biomass using maleic acid are provided. The use of maleic acid results in rapid delignification of the biomass with excellent selectivity in preserving cellulose at atmospheric pressure and temperatures below the boiling point of the acid solution, e.g. at temperatures of 120° C. or less, at or above the minimal hydrotrope concentration (MHC) (25 wt. %). Both the dissolved lignin and the lignin remaining on the cellulosic solids have low degrees of condensation, which is critical to lignin valorization and bleaching of the cellulosic fraction derived from the fractionation.

Various embodiments of the inventions described herein are based, at least in part, on the discovery that maleic acid is capable of efficiently solubilizing and carboxylating hydrophobic lignin in lignocellulosic biomass that is substantially unprocessed at low temperatures in a short period of time with a low degree of lignin condensation. As such, a low-energy, low-cost and efficient lignocellulosic biomass fractionation process can be carried out in aqueous solution, at low temperatures and atmospheric pressures.

The fractionation produces a solid fraction that contains mainly carboxylated cellulose and some hemicelluloses and a liquid fraction that contains dissolved carboxylated lignin and some hemicellulosic sugars. The solid fraction can be used to produce wood fibers, with or without bleaching, and/or cellulose micro- or nanomaterials, and/or sugars (through hydrolysis), and/or valuable chemicals, such as furfural. The cellulose micromaterials and nanomaterials include lignocellulosic microfibrils (LCMFs) or lignocellulosic nanofibrils (LCNFs) with controllable lignin contents on their surfaces (e.g., coated via precipitation) or in their cellulosic matrices (containing native lignin) from the fractionated solids. The solubilized lignin in the liquid fraction can be separated as lignin nanoparticles through the precipitation of solubilized lignin by diluting the spent acid solution with water to a concentration below the MHC of the maleic acid. The obtained lignin nanoparticles (LNPs) comprise oblate spheroids with tunable morphology and surface properties. Some embodiments of the LNPs have diameters ranging from, for example, 150~3000 nm and thicknesses ranging from, for example, 3~50 nm. The properties of the lignin LNPs can be tailored by controlling the pretreatment conditions of the biomass and the diluting factors of the spent maleic acid solutions.

Lignocellulosic Biomass: As used herein, the term lignocellulosic biomass refers to materials from plant cell wall that primarily includes lignin and hemicelluloses, as well as cellulose. Lignocellulosic biomass may be, for example, wood or non-woody biomass, such grasses, and agriculture crop stems or stalks. Wood biomass can be a hardwood, such as birch, or a softwood or a mixture thereof. The wood may, optionally, be debarked and provided in milled or chip form. However, for the production of wood fibers, wood chips may be more suitable. Examples of non-woody biomass include switchgrass, wheat straw, begasse, sorghum stalks, and corn stover. Lignocellulosic biomass is substantially unprocessed and, therefore, does not include bleached wood pulp. However, some minor pre-processing of the starting lignocellulosic biomass, such as debarking and size-reduction is permissible. The lignin content of the lignocellulosic biomass will depend on the natural lignocellulosic biomass being used. For example, raw wood biomass typically has a lignin content of greater than 20 wt. %, including greater than 25 wt. %, while non-woody biomass, may have a lower lignin content.

Lignocellulose Nanocrystals (LCNCs): As used herein, the term LCNC refers to elongated rod-like crystalline lignin-containing cellulose nanoparticles. LCNCs comprise cellulose chains produced from lignocellulosic biomass via fractionation. LCNCs can be in the form of a single cellulose crystallite or a bundle of cellulose crystallites, and may or may not contain hemicelluloses. LCNCs are generally characterized by lengths in the range from about 60 nm to about 1000 nm; widths in the range from about 5 nm to about 50 nm; and corresponding aspect ratios in the range from about 1 to about 200.

Lignocellulose Nanofibrils (LCNFs): As used herein, the term LCNF refers to long flexible fiber-like lignin-containing cellulose nanoparticles. LCNFs can be branched or unbranched and can take the form of a network of flexible fiber-like nanoparticles. LCNFs comprise cellulose, hemicelluloses, and lignin. The fiber-like lignocellulose particles are generally characterized by lengths in the range from about 100 nm to about 5,000 nm; widths in the range from about 5 nm to about 200 nm; and corresponding aspect ratios in the range from about 2 to about 1,000.

Lignocellulose Fibers (LCFs): As used herein, the term LCF refers to lignin-containing cellulose particles. LCFs comprise cellulose, hemicelluloses, and lignin. LCFs are generally characterized by lengths in the range from about 0.05 mm to about 3 mm; widths in the range from about 5 μm to about 50 μm; and corresponding aspect ratios in the range from about 2 to about 500.

Lignocellulose Microfibers (LCMFs): As used herein, the term LCMF refers to lignin-containing cellulose microparticles. LCMFs comprise cellulose, hemicelluloses, and lignin. LCMFs are characterized by lengths in the range from about 5 μm to about 100 μm; widths in the range from about 0.1 μm to about 10 μm; and corresponding aspect ratios in the range from about 2 to about 500.

Lignocellulosic Solid Residues (LCSR): As used herein, the term LCSR refers to a solid material composed of LCFs, LCMFs, or a combination thereof. In the present methods, LCSRs are part of the solid material remaining after the biomass fractionation.

Lignin Nanoparticles (LNPs): As used herein, the term LNP refers to lignin nanoparticles. LNPs can be in the form of single lignin macro molecule or aggregates of lignin macro molecules. LNPs are generally characterized by dimensions in the range from 1 nm to 10 μm (e.g., from 10 nm to 500 nm) and may have an oblate spheroid shape.

For the purposes of this disclosure, lignin with a low degree of condensation is defined as lignin having a β-O-4-aryl-ether linkage content that is not substantially reduced relative to the β-O-4-aryl-ether linkage content of the lignocellulosic biomass from which it was derived. The β-O-4-aryl-ether linkage content can be measured using the procedures described in many prior arts such as $^{13}C$-$^{1}H$ 2D nuclear magnetic resonant (NMR) spectroscopy (Cai et al., 2020). By way of illustration, the dissolved lignin resulting from some embodiments of the methods described herein may have a degree of condensation (i.e., a reduction in β-O-4-aryl-ether linkage content) of less than 30%, less than 25%, or less than 20% (e.g., a degree of condensation in the range from 5% to 30%). The degree of condensation for the lignin remaining in the solids after the maleic acid treatment is generally even smaller.

The degree of carboxylation of the lignin, the solid residues, and/or the downstream products produced from the solid residues can be measured in terms of their carboxyl group content. Depending on the particular reaction conditions used, the lignin, solid residues, and/or downstream products (e.g., LCNFs) can have a carboxyl group (COOH) concentration of at least 0.05 mmol/g. For example, carboxyl group concentrations in the range from 0.050 mmol/g to 0.25 mmol/g can be provided.

Generally, these methods are conducted under conditions that can be characterized using a combined delignification factor (CDF), as described in greater detail below, of 200 or less, including 150 or less, and further including 100 or less. CDF is a function of acid concentration, reaction temperature, and reaction time. The proper CDF values for achieving desired delignification may vary with the lignocellulosic biomass used. More detail with regard to methods for measuring the CDF for a given set of conditions is provided in the Examples.

The use of maleic acid to solubilize lignin in biomass fractionation is advantageous because the maleic acid esterifies and carboxylates the lignin, making fractionation more efficient. With maleic acid, the process can be conducted at low temperatures using a very short reaction time. By way of illustration, various embodiments of the lignocellulosic biomass fractionation are carried out at temperatures of no greater than 120° C. This includes embodiments of the lignocellulosic biomass fractionation that are carried out at temperatures of no greater than 100° C. and further includes embodiments of the lignocellulosic biomass fractionation that are carried out at temperatures of no greater than 80° C. For example, the lignocellulosic biomass fractionation can be carried out at temperatures in the range from 70° C. to 120° C., including temperatures in the range from 80° C. to 100° C. However, temperatures outside of these ranges can be used, depending on the desired degree of lignin dissolution. By way of further illustration, various embodiments of the lignocellulosic biomass fractionation can be completed in a reaction time of 5 hours or less. This includes embodiments of the lignocellulosic biomass fractionation that are completed in a reaction time of, 3 hours or less, 1 hour or less, or 30 minutes or less. For example, the lignocellulosic biomass fractionation can be carried out for a reaction time in the range from 10 minutes to 90 minutes, including reaction times in the range from 15 minutes to 60 minutes, and further including in the range from 10 minutes to 30 minutes. However, reaction times outside of these ranges can be used, depending on the desired degree of lignin dissolution. As used herein, the reaction time refers to the time between the onset of the solubilization of the lignin in the biomass by the maleic acid and the cessation of the lignin solubilization when the maleic acid concentration in the fractionation solution is brought below its minimal hydrotrope concentration. Thus, the solubilization of lignin using maleic acid can be terminated by decreasing the acid concentration to below about 25 wt. %.

In the lignocellulosic biomass fractionation solution, the maleic acid has a concentration above its minimum hydrotrope concentration, so that it solubilizes and carboxylates lignin, which is hydrophobic, in the fractionation solution. Generally, the maleic acid has a concentration that is significantly greater than the minimum hydrotrope concentration in order to enhance lignin solubilization. By way of illustration, in various embodiments of the lignocellulosic biomass fractionation method, the fractionation solution has a maleic acid concentration of at least 25% (or above MHC). This includes embodiments of the methods in which the fractionation solution has a maleic acid concentration of at least 30 wt. % or greater, 50% wt. % or greater, and 60 wt. % or greater. For example, maleic acid concentrations in the range from about 30% to about 80%, including in the range from about 50% to about 60%, can be used. However, concentrations outside of these ranges can be used, depending upon the desired degree of lignin dissolution.

The lignocellulosic biomass fractionation process can solubilize the majority of the lignin in a lignocellulosic biomass sample without the need for an initial pulping to reduce the lignin content prior to the maleic acid treatment. In various embodiments of the lignocellulosic biomass fractionations, at least 10% of the lignin in the biomass is solubilized during the fractionation. This includes embodiments of the fractionations that solubilize at least 45 wt. %, at least 50 wt. %, and at least 55 wt. % of the lignin in the biomass. For example, 40 wt. % to 60 wt. % of the lignin can be solubilized. However, percentages of lignin solubilization outside of these ranges can also be achieved. The solubilization of the lignin can also be quantified in terms of grams of lignin dissolved per 100 g of solution. In some embodiments of the lignocellulosic biomass fractionation, at least 2 g lignin/100 g of solution is dissolved.

Reaction temperatures, times, and maleic acid concentrations can be selected from within the ranges recited above to provide an appropriate CDF for a given fractionation process. By way of illustration, in some embodiments, the methods for producing minimally condensed solubilized lignin are carried out at temperatures of 100° C. or lower, for times of 30 minutes or shorter, using maleic acid concentrations of 60 wt. % or lower. However, other combinations of reaction conditions can be employed. By way of further illustration, the methods can be carried out at temperatures in the range from 70° C. up to the boiling point of the maleic acid hydrotrope solution, e.g., approximately 120° C., depending on the maleic acid concentration of the solution, for times in the range of approximately 30 to 60 minutes to avoid any significant lignin condensation, at acid concentrations in the range from 25 wt. % to 40 wt. %. The methods can also be carried out at temperatures in the range from 80° C. to 110° C., for times of 10 minutes to 30 minutes, at acid concentrations in the range from 40 wt. % to 85 wt. %. It is the combination of temperature, reaction time, and acid concentration (or acidity or pH, when strong acid is supplemented to facilitate delignification) that determines whether or not the resultant AHL is condensed. In other words, to produce an uncondensed lignin, one can use a high acid concentration (≥40 wt. %), but under a low temperature (≤100° C.) and for a short time (≤30 min), or an elevated temperature (>100° C.) but using a low acid concentration (≤40 wt. %) and short time (≤30 min). These conditions may be used when fractionation is conducted in a batch mode. Flow-through fractionations can also be carried out. Flow-through fractionation can substantially reduce the contact time between the maleic acid and the dissolved lignin; to compensate for this, slightly higher acid concentrations (e.g., >40 wt. %) and reaction temperatures (e.g., >100° C.) can be used without causing substantial condensation of dissolved lignin. The rapid removal of reaction products in flow-through fractionation can facilitate delignification. As such, a shorter reaction time can be used to achieve delignification equivalent to that of a batch process, which also can reduce the degree of condensation of the lignin retained on the undissolved cellulosic solids.

FIG. 1 is a schematic diagram illustrating various embodiments of a lignocellulosic biomass processing method that can be carried out at low temperature and ambient pressure. The processing method includes a lignocellulosic biomass pre-treatment, followed by lignocellulosic biomass fractionation with maleic acid and, optionally, post-fractionation processing that can be carried out for producing fibers, and/or LCNF or LCMF, and/or sugars, and/or LNP with recovery of acid. In a lignocellulosic biomass pre-treatment step, lignocellulosic biomass 102, such as wood, is size-reduced 104 using, for example, low mechanical energy input disk milling conducted at temperatures above lignin glass transition temperature using steam. Another pre-treatment step that can be included in the process is prehydrolysis using hot water to improve hemicellulose removal and delignification. The size-reduced, fibrillated, and/or prehydrolyzed lignocellulosic biomass is then fractionated 106 using maleic acid as a hydrotrope 108 for the lignin in the biomass at a low temperature (for example, approximately 120° C. or lower) for a short time (e.g., 30 minutes to two hours). After subsequent filtration and, optionally, washing 110, the spent acid solution from the lignocellulosic biomass fractionation 106 can be cycled back to the fractionation and directly reused 112. After several runs, dissolved solids, such as lignin and sugars, accumulate in the spent acid solution. These may be removed to further reuse the acid.

Dissolved lignin in the filtrate can be easily removed by precipitation initiated through dilution with water 114. The diluted spent liquor can then be re-concentrated to convert dissolved sugars, such as xylose, into furans, such as furfural, through dehydration (e.g., evaporation) 116 using the maleic acid in the liquor as a catalyst. Re-concentration can also facilitate the removal of excess maleic acid 118 from the system through crystallization 116 when desirable. The furans 122 can be separated through distillation and dehydration. The remaining acid solution can then be cycled back to reused in the lignocellulosic biomass fractionation 106. The separated and subsequently washed water-insoluble solids contain LCSRs, and LCNC. Optionally, the LCNCs can be separated from the LCSRs by dialysis. The LCSR, with or without separating LCNC, can be used for producing chemical pulp fibers such as dissolving pulps 124 after bleaching 126, LCMF and/or LCNF 128 with mechanical fibrillation 130, or sugars 132 through (enzymatic) hydrolysis 134. The relative amount of LCNFs or LCMFs produced can be controlled by the severity of biomass fractionation. Low severity fractionation conditions tend to favor the production of long LCNFs.

Another aspect of the inventions provides methods for the production of LNPs with controllable sizes and shapes directly from the spent liquor from the biomass fractionation simply by precipitation after water dilution, as illustrated in FIG. 1. Processing conditions that can be used to control the size and morphology of the LNPs include the rate at which the spent fractionation solution is diluted and the severity of the biomass fractionation reaction conditions. The pH of the solution can also be used to tailor LNP size, whereby changing the pH of the spent liquor from the biomass fractionation to a low value (e.g., ≤3) or a high value (e.g., ≥10) results in a larger LNP size.

As used in this disclosure, any concentrations that are provided as a percentage (%) refer to a weight percentage (wt %), unless otherwise indicated.

Other principal features and advantages of the invention will become apparent to those skilled in the art upon review of the following drawings, the detailed description, and the appended claims.

EXAMPLES

Materials Used

Maleic acid (MA) anhydrate was purchased from Sigma-Aldrich (St. Louis, Mo.).

Birch logs were obtained from northern Wisconsin. The logs were hand peeled to remove bark and then chipped at the USDA Forest Products Laboratory, Madison, Wi. The chips were screened with 1-1/4" square holes. Oversized chips were re-chipped to increase recovery. The resultant wood chips were then hammer-milled. The materials passing through a 4.8 mm screen were collected. A part of the hammer-milled material was further size-reduced to 30 mesh using a Wiley mill. The size reduced woody materials were air-dried at room temperature to moisture content of 15% and then stored in a refrigerator for later use.

Wheat straw, chopped to ~12 mm length, was used as received from a private company.

Switchgrass was complimentarily provided by the Department of Biological Systems Engineering, University of Wisconsin-Madison. The switchgrass was Wiley-milled with a 1-cm mesh size screen. The materials that passed the screen were used.

Example 1: Wood Fractionation Using Concentrated Maleic Acid Solution

Aqueous MA solutions of 30-70 wt. % concentrations were prepared in 100 mL glass bottles by solubilizing desired amounts of MA in 30 mL of deionized (DI) water. Each bottle was placed on a temperature-controlled shaking bed (Model 4450, Thermo Scientific, Waltham, Ma.) shaking at 250 rpm to promote the dissolution of MA. All fractionations were carried out according to the experimental schematic flow diagram shown in FIG. 1. Three g in oven dry (OD) weight of the air-dried birch was placed into 30 g of prepared MA solution with continuous shaking at a selected temperature for a designated period of time. The fractionation runs were labeled as MxxTyytzz to represent MA concentration of xx wt. % at yy ° C. for zz min as listed in Table 1. At the end of fractionation, the spent MA liquor was separated through filtration. The solids were washed three times using DI water. The resultant washed water insoluble solids (WIS) were analyzed for chemical composition. The filtrate was diluted using deionized (DI) water to 15 wt. % MA concentration.

Example 2: Fractionated Solids of Birch Wood

The chemical compositions of the original, as well as the MA fractionated solids of birch, were analyzed by the Analytical Chemistry and Microscopy Lab (ACML) at the US Forest Service, Forest Products Lab, as described previously (Davis, 1998; Luo et al., 2010). As listed in Table 1, concentrated MA solution was able to solubilize a substantial (up to 55%) amount of birch wood lignin at 100° C. or lower. Dissolution of xylan was also substantial. Glucan loss, however, was minimal. A reaction severity can be used to achieve desired fractionation by adjusting the reaction severity as listed in Eqs. (1) and (2) rather than individual reaction conditions. This is important in process scale-up for producing pulp fibers, and especially for dissolving pulp fibers, which require high cellulose yield, good strength, and minimal lignin and hemicelluloses contents.

$$L_R = (1-\theta'-\theta'_R)e^{-CDF} + \theta' \cdot e^{-f \cdot CDF} + \theta'_R \tag{1a}$$

with $$CDF = \exp\left(\alpha' - \frac{E'}{RT} + \beta'C\right)C \cdot t \tag{1b}$$

$$X_R = (1-\theta31\ \theta_R)e^{-CHF} + \theta \cdot e^{-f \cdot CHF} + \theta_R \tag{2a}$$

with $$CHF = \exp\left(\alpha - \frac{E}{RT} + \beta C\right)C \cdot t \tag{2b}$$

where $L_R$ and $X_R$ are fractions of lignin and xylan retained on WIS based on the amount of lignin and xylan in wood, respectively. $\theta'$ and $\theta$ are the fractions of bulk fast solubilization lignin and xylan, respectively; $\theta'_R$ or $\theta_R$ are unsolulable residue lignin and xylan; $f'$ or $f$ are the ratio of lignin or xylan solubilization between the slow and bulk fast lignin or xylan; $\alpha'$, $\alpha$ and $\beta'$, $\beta$ are adjustable parameters; E' and E are activation energy; R is the universal gas constant (8.314 J/mol/K); T is temperature in kelvins; C is initial MA concentration in mol/L; and t is dissolution time in min.

TABLE 1

Chemical compositions of birch along with MA fractionated WIS samples. The numbers in the parentheses are component retained on WIS based on component in unfractionated lignocelluloses.

| Sample | CDF | WIS yield (%) | K. Lignin (%) | Galactan (%) | Glucan (%) | Xylan (%) | Mannan (%) |
|---|---|---|---|---|---|---|---|
| Birch | | 100 | 19.5 | 1.31 | 39.96 | 22.99 | 1.44 |
| M30T80t60 | 1 | 87.2 | 19.7 (88.2) | 0.6 | 41.6 (90.8) | 22.8 (86.6) | 1.3 (8.03) |
| M50T80t60 | 18 | 76.4 | 19.3 (75.4) | 0.6 | 47.3 (90.4) | 19.3 (64.0) | 1.6 (83.6) |
| M70T80t60 | 443 | 66.0 | 15.9 (53.8) | 0.6 | 51.2 (84.6) | 14.8 (42.5) | 1.5 (70.9) |
| M50T70t60 | 4 | 88.5 | 16.0 (72.7) | 1.1 | 39.7 (87.9) | 22.5 (86.6) | 1.2 (73.5) |
| M60T80t60 | 88 | 71.9 | 18.5 (68.1) | 0.6 | 47.5 (85.4) | 18.0 (56.4) | 1.5 (72.7) |
| M50T90t60 | 77 | 65.7 | 18.4 (61.9) | 0.6 | 50.5 (83.0) | 15.6 (44.5) | 0.8 (34.4) |
| M50T80t30 | 9 | 86.0 | 18.4 (81.3) | 0.6 | 41.2 (88.7) | 21.8 (81.6) | 1.4 (84.6) |
| M50T80t60 | 18 | 80.8 | 18.9 (78.3) | 0.5 | 42.8 (86.6) | 19.9 (69.2) | 1.5 (82.1) |
| M50T80t90 | 28 | 72.1 | 18.7 (69.0) | 0.7 | 49.1 (88.6) | 16.6 (51.9) | 1.5 (73.1) |
| M50T80t120 | 37 | 75.5 | 19.0 (73.4) | 0.7 | 48.2 (91.0) | 18.1 (59.6) | 1.4 (71.2) |
| M50T100t30 | 151 | 64.7 | 15.4 (51.5) | 0.0 | 57.4 (92.9) | 11.0 (31.0) | 1.4 (63.0) |
| M50T100t60 | 302 | 55.4 | 17.5 (49.7) | 0.0 | 52.2 (72.3) | 14.2 (34.3) | 1.5 (57.0) |
| M50T100t90 | 453 | 58.5 | 16.0 (48.1) | 0.0 | 60.1 (87.9) | 10.7 (27.3) | 1.3 (52.4) |
| M50T100t120 | 603 | 53.3 | 16.0 (43.7) | 0.0 | 55.8 (74.4) | 11.8 (27.3) | 1.1 (39.0) |
| M70T80t30 | 221 | 64.1 | 14.4 (47.3) | 0.0 | 53.6 (86.0) | 14.6 (40.6) | 1.4 (61.8) |
| M60T90t30 | 185 | 64.0 | 15.8 (51.9) | 0.0 | 54.3 (87.0) | 14.0 (39.0) | 1.5 (64.9) |
| M60T90t60 | 371 | 58.9 | 14.6 (44.2) | 0.0 | 55.2 (81.4) | 13.2 (33.7) | 1.5 (60.8) |
| M60T70t120 | 39 | 70.6 | 17.5 (63.3) | 0.0 | 47.2 (83.3) | 15.9 (48.7) | 1.1 (53.4) |
| M60T110t30 | 547 | 62.9 | 16.2 (52.3) | 0.0 | 55.2 (86.9) | 15.9 (43.5) | 1.9 (83.0) |
| M60T120t30 | 1857 | 55.4 | 12.9 (36.6) | 00 | 61.3 (85.0) | 13.8 (33.3) | 1.5 (57.7) |

Figure 2B:
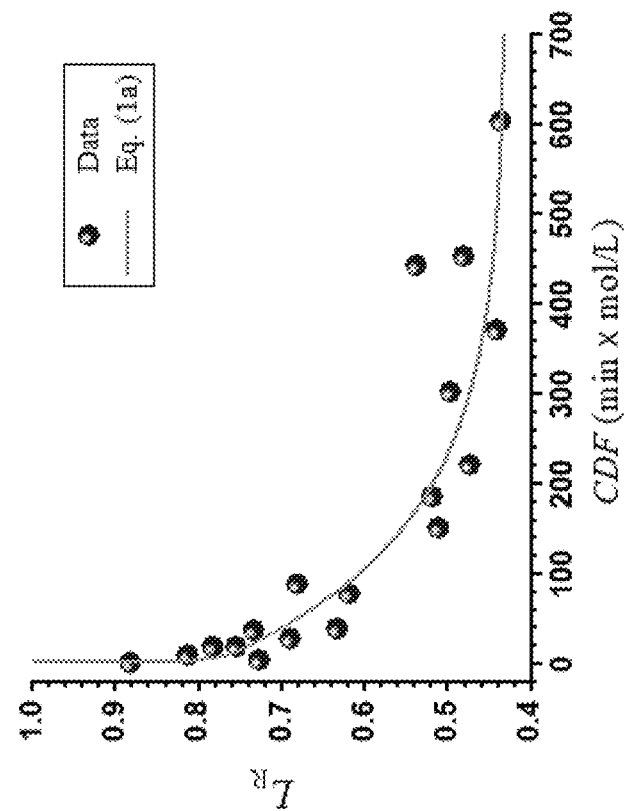
FIGS. 2A-2B. Experimentally measured birch wood xylan (FIG. 2A) and lignin (FIG. 2B) dissolutions by maleic acid fractionation under different conditions along with their predictions based on reaction-severity-based reaction kinetics.
Figure 2A:
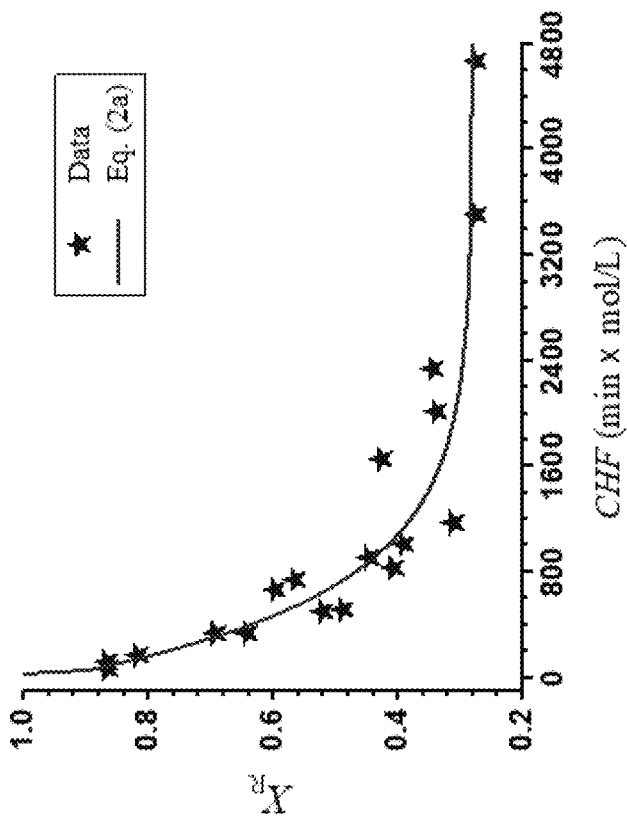

Eqs. (1) and (2) fit to the experimental data very well for birch, as shown in FIGS. 2A and 2B. The fitting parameters are listed in Table 2. Overall, cellulose dissolution was low as confirmed by compositional analyses of WISs (Table 2). Depending on fractionation severity, the dissolved xylan can be in the form of xylooligomers (low xylose concentration) or mainly xylose at high severities as listed in Table 3. Acetic acid concentration in the spent liquor was below 4.5 g/L. Furfural from dehydration of xylose was not detectable in the spent liquor because maleic acid has low acidity.

TABLE 2

Fitting parameters in Eqs. (1) and (2) from xylan and lignin yield data listed in Table 1.

| Parameter | Unit | Xylan | Lignin |
|---|---|---|---|
| $\alpha, \alpha'$ | None | 34.5 | 44.1 |
| $\beta, \beta'$ | L/mol | 0.704 | 1.621 |
| E, E' | J/mol | 107,000 | 153,000 |
| $\theta, \theta'$ | None | 0.6668 | 0.3546 |
| f, f' | None | 0.0016 | 0.0070 |
| $\theta_R, \theta'_R$ | None | 0.28 | 0.43 |

TABLE 3

Species concentrations in maleic acid fractionated spent liquor.

| Liquor Sample | Glucose (g/L) | Xylose (g/L) | Formic acid (g/L) | Acetic acid (g/L) |
|---|---|---|---|---|
| M30T80t60 | 0.10 | 0.72 | 1.45 | 1.81 |
| M50T80t60 | 0.22 | 2.93 | 4.18 | 3.17 |
| M60T80t60 | 0.29 | 6.15 | 7.26 | 1.94 |
| M70T80t60 | 0.30 | 12.5 | 25.95 | 2.30 |
| M50T70t60 | 0.22 | 0.57 | 1.43 | 1.11 |
| M50T90t60 | 0.34 | 4.74 | 6.77 | 2.79 |
| M50T80t30 | 0.14 | 0.65 | 1.92 | 1.69 |
| M50T80t60 | 0.24 | 3.21 | 4.37 | 1.79 |
| M50T80t90 | 0.31 | 3.99 | 5.13 | 2.25 |
| M50T80t120 | 0.36 | 4.23 | 5.69 | 2.57 |
| M50T100t30 | 0.17 | 9.46 | 9.50 | 3.64 |
| M50T100t60 | 0.87 | 17.70 | 23.01 | 4.50 |
| M50T100t90 | 0.63 | 17.79 | 20.78 | 3.10 |
| M50T100t120 | 0.81 | 18.10 | 21.11 | 4.35 |
| M70T80t30 | 0.52 | 9.25 | 10.53 | 3.39 |
| M60T90t30 | 0.57 | 9.73 | 8.26 | 2.26 |
| M60T90t60 | 0.53 | 14.11 | 14.08 | 3.92 |
| M60T70t120 | 0.34 | 7.77 | 7.82 | 3.15 |
| M60T110t30 | 0.5 | 12.3 | | |
| M60T120t30 | 1.1 | 14.9 | | |

Example 3: Minimal Hydrotrope Concentration (MHC)

Figure 3:
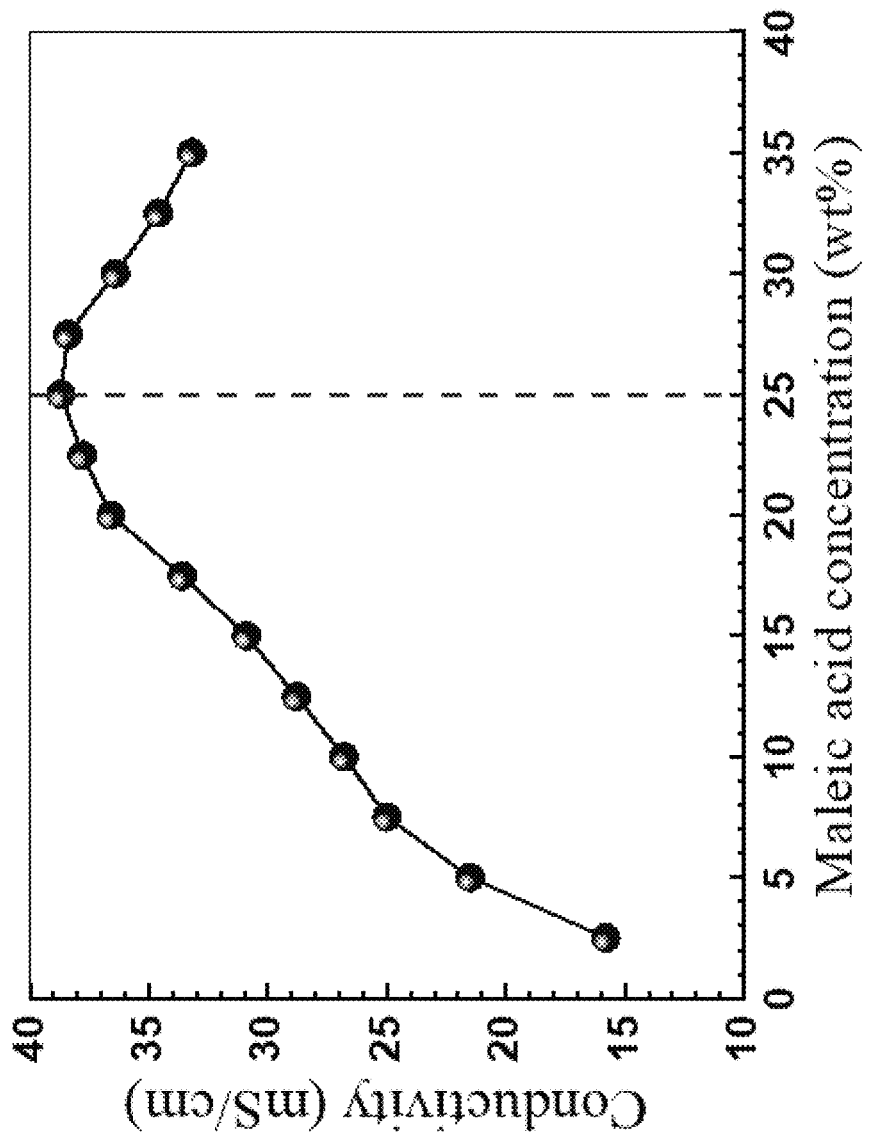
FIG. 3. Conductivity of maleic acid solutions under different concentrations. The concentration corresponding to the peak conductivity (discontinuity point) is the minimal hydrotropic concentration (MHC).

Hydrotropes aggregate above their minimal hydrotrope concentration (MHC). A high MHC is good for reducing water usage in dilution to precipitate the solute. The conductivity of maleic acid solution in a range of concentrations was measured to determine its MHC. The transition point in the measured conductivity curve was 25 wt. %, as shown in FIG. 3, suggesting maleic acid has a MHC of 25 wt. %. If a maleic acid concentration of 50 wt. % is used in fractionation, a dilution factor of 2 is sufficient to precipitate lignin.

Example 4: Sugar Production from Fractionated Solids

Figure 4A:
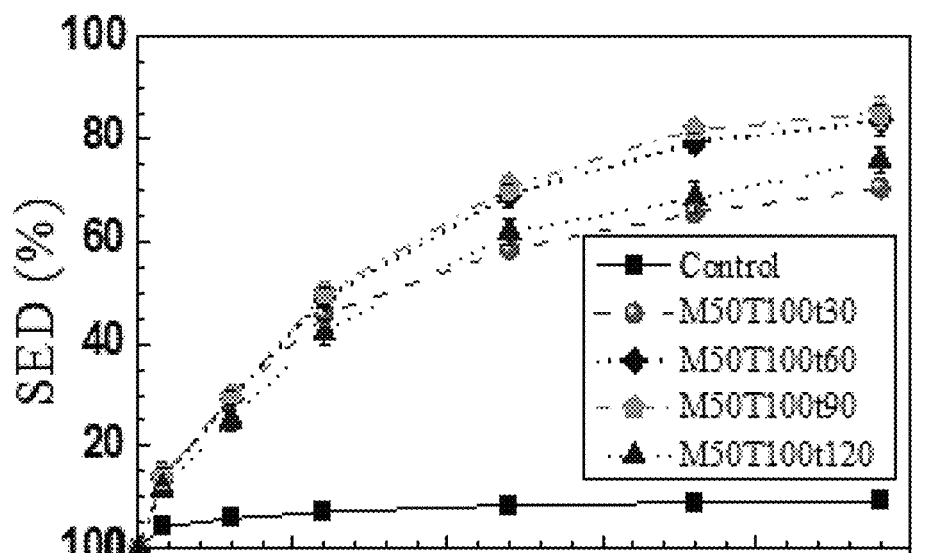
FIGS. 4A-4C. Effects of maleic acid hydrotropic fractionation conditions on fractionated water insoluble solids (WIS) enzymatic digestibility (Cellulase CTec3 loading=10 FPU/g glucan; buffer pH=5.5 for FIGS. 4A-4C).
Figure 4B:
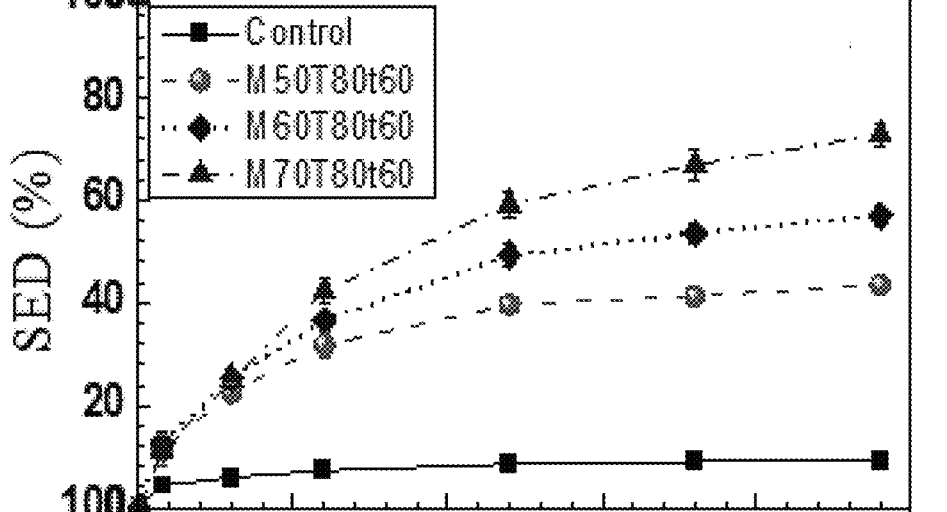
Figure 4C:
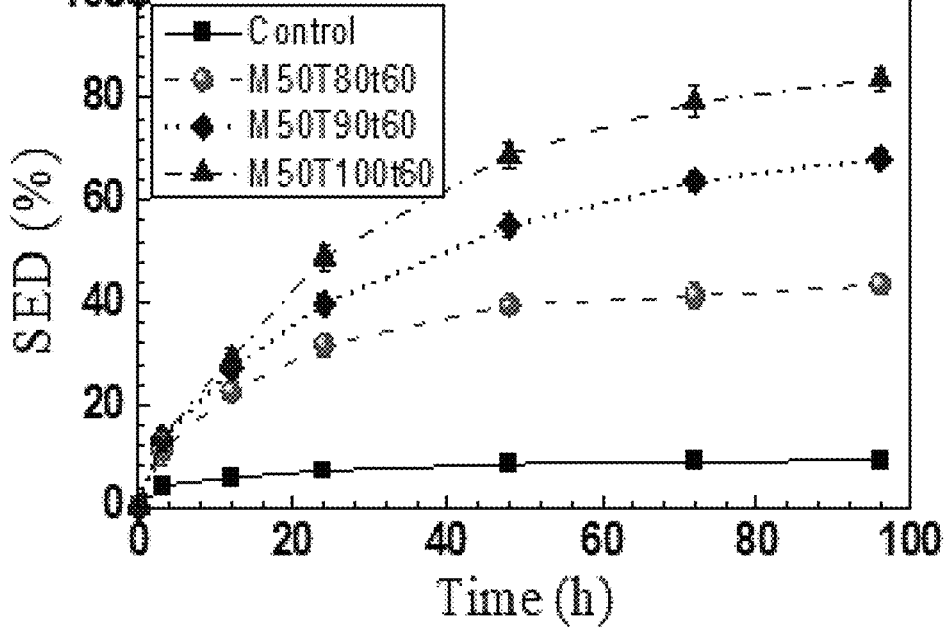

The fractionated WISs of birch had excellent enzymatic digestiblities. Therefore, the present fractionation method using maleic acid can be applied to producing sugars/biofuels from lignocelluloses at low temperatures and atmospheric pressure with short reaction times. Commercial cellulase (CTec3) was used to enzymatically hydrolyze the maleic acid fractionated WIS at a relatively low loading of 10 FPU/g glucan in an acetate buffer of pH 5.5. Substrate cellulose enzymatic digestibility (SED) of approximately 85% was achieved for WIS from M50T100t90 as shown in FIG. 4A. SED was near 80% even with a shorter fractionation time of 30 min. It appears that a too-long fractionation of 120 min may have condensed lignin, which resulted in a reduced accessibility of cellulose and therefore a reduced SED compared with the WIS from M50T100t60 or M50T100t90. The optimum fractionation should be approximately 75 min at 50% acid concentration and 100° C. based on the results shown in FIG. 4A. At a low fractionation temperature, such as 80° C., an increase in maleic acid concentration increased SED, as shown in FIG. 4B, due to increased removal of lignin and hemicelluloses (Table 1). Similar observations can be made on the effect of fractionation temperature, as shown in FIG. 4C. SED was doubled to approximately 85% when lignin and xylan removal were increased from approximately 25 and 35% to approximately 50 and 65%, respectively, and when fractionation temperature was increased from 80° C. to 100° C. using acid concentration of 50 wt. % for 60 min.

Figure 5A:
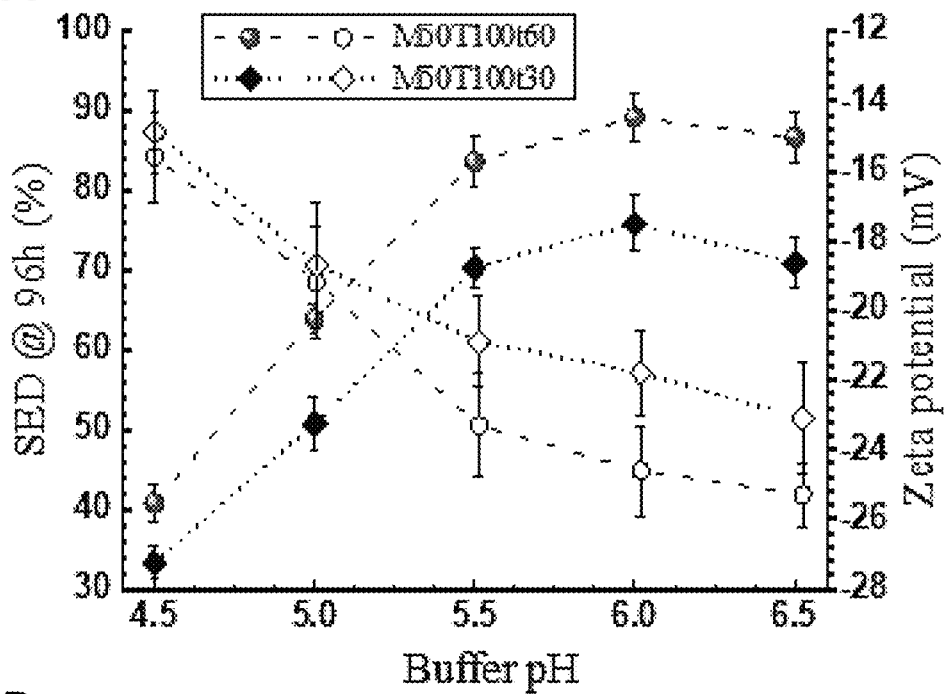
FIGS. 5A-5B Effects of buffer solution pH (FIG. 5A) and cellulase loading (FIG. 5B) on enzymatic hydrolysis digestibility of maleic acid fractionated birch water insoluble solids (WIS).
Figure 5B:
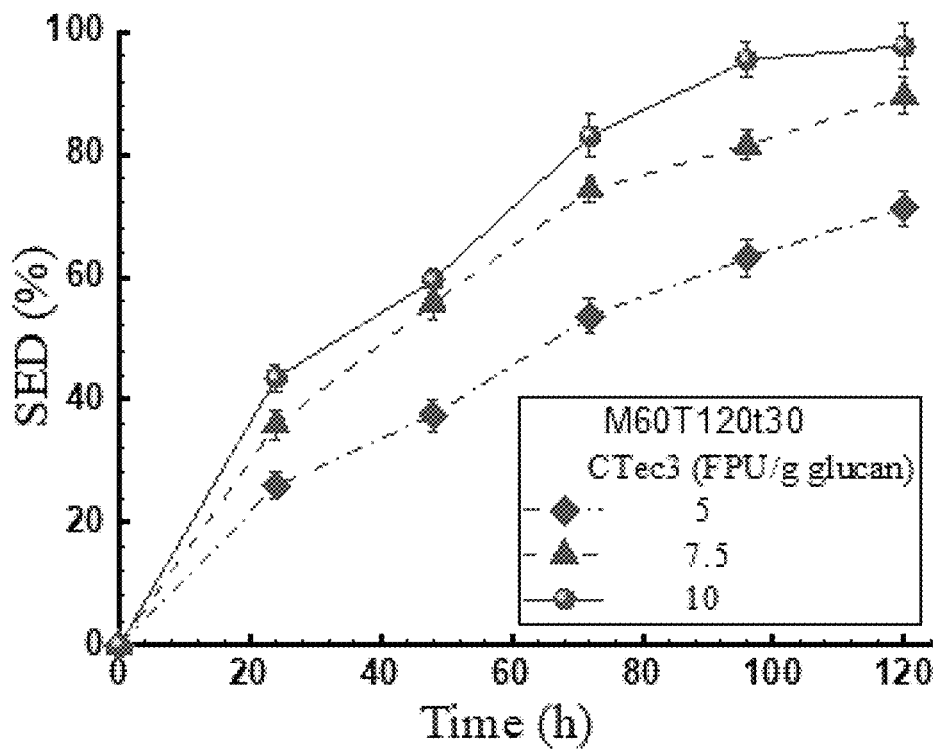

Non-productive cellulase binding to lignin can reduce cellulase activity. Using an elevated pH greater than the isoelectric point (pI) of the cellulase during enzymatic hydrolysis can not only make the cellulase slightly negatively charged, it can also make the substrate lignin more negatively charged when the lignin contains charge groups, such as -COOH and -$HSO_3$. As a result, an elevated pH can reduce non-productive cellulase binding to lignin to enhance enzymatic saccharification. As shown in FIG. 5A, an elevated buffer pH increased the substrate charge (more negative). The maximal enzymatic saccharification yield was obtained at buffer pH 6.0. The results shown in FIGS. 4A-C can be further improved by 5% by using buffer pH 6.0. This allows the use of lower cellulase loading, as shown in FIG. 5B. For WIS from treatment at M60T120t30, an SED of approximately 90% can be achieved at CTec3 loading of 7.5 FPU/g glucan. Even at 5 FPU/g glucan, SED of approximately 80% can be expected with saccharification time extending to 140 h.

Solubilized sugars in the spent acid solution, mainly hemicellulosic sugars, can be converted into furan using the maleic acid in the spent liquor without additional catalyst.

Example 5: Production of Lignocellulosic Nanofibrils from Birch Wood

Figure 7:
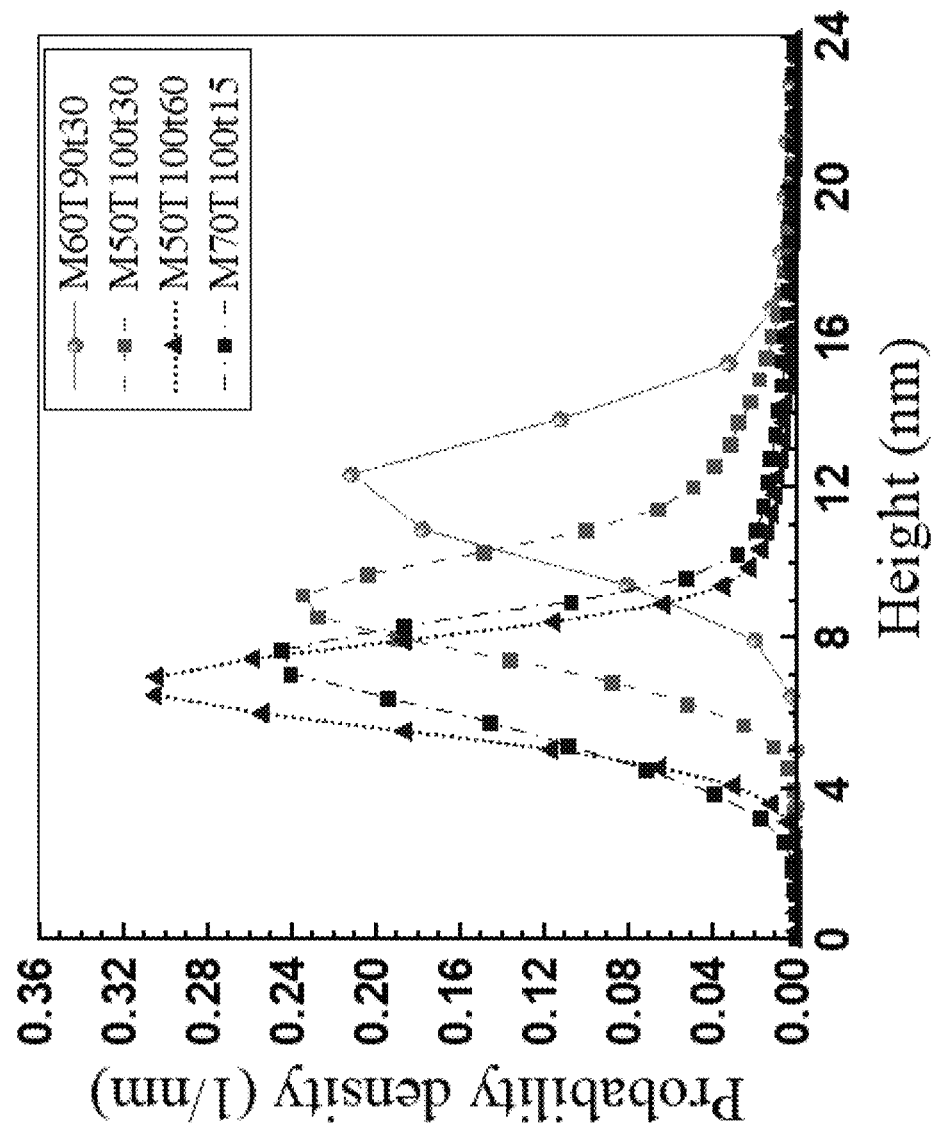
FIG. 7. Maleic acid hydrotropic fractionation conditions on resultant birch wood LCNF fibril height distribution probability density from AFM topographical measurements.
Figure 8:
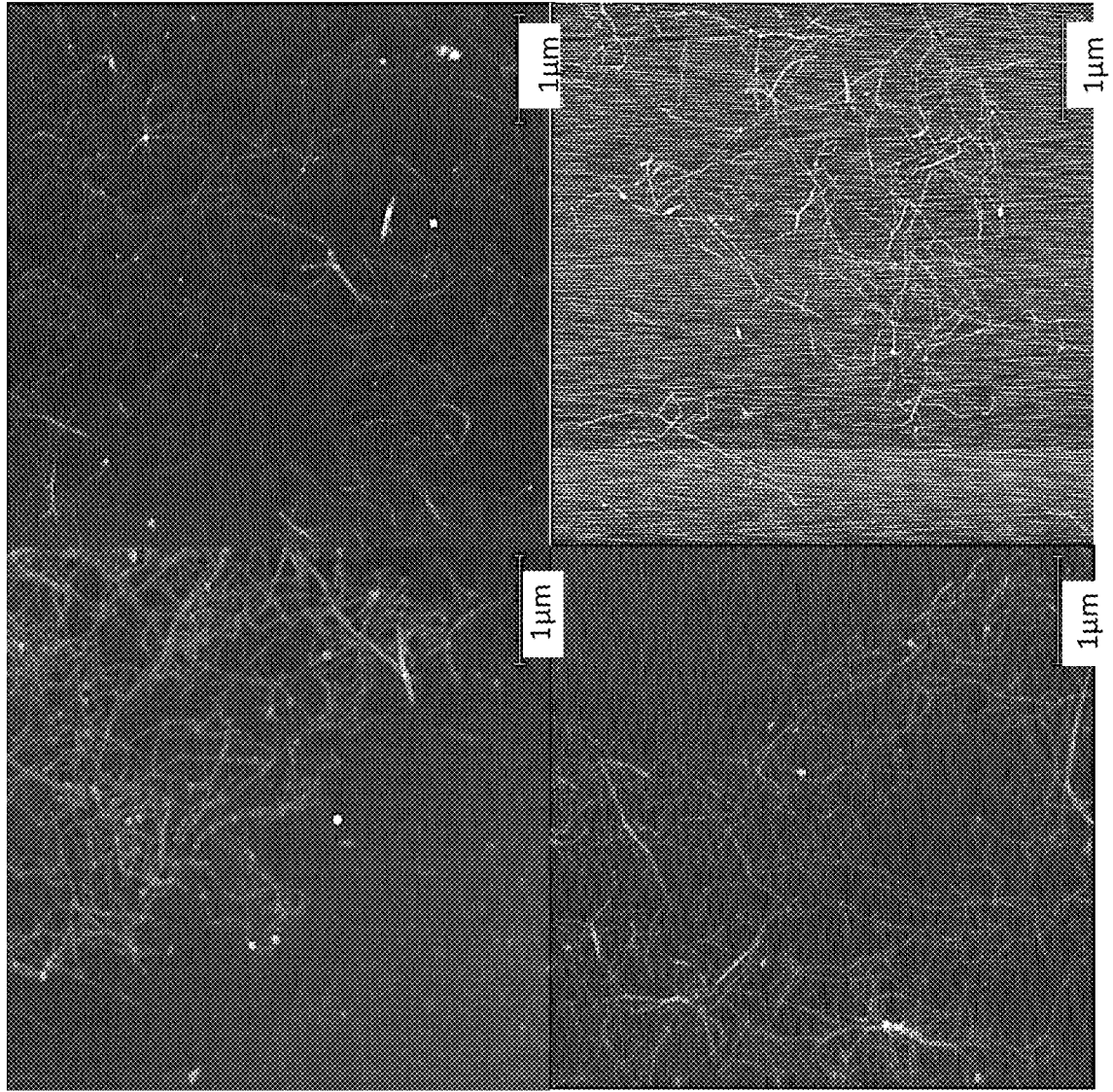
FIGS. 8A-8D. The extent of mechanical fibrillation on resultant morphology of lignin-containing cellulose nanofibrils (LCNFs) from birch WIS under fractionation condition M50T100t30 observed by AFM.
Figure 9:
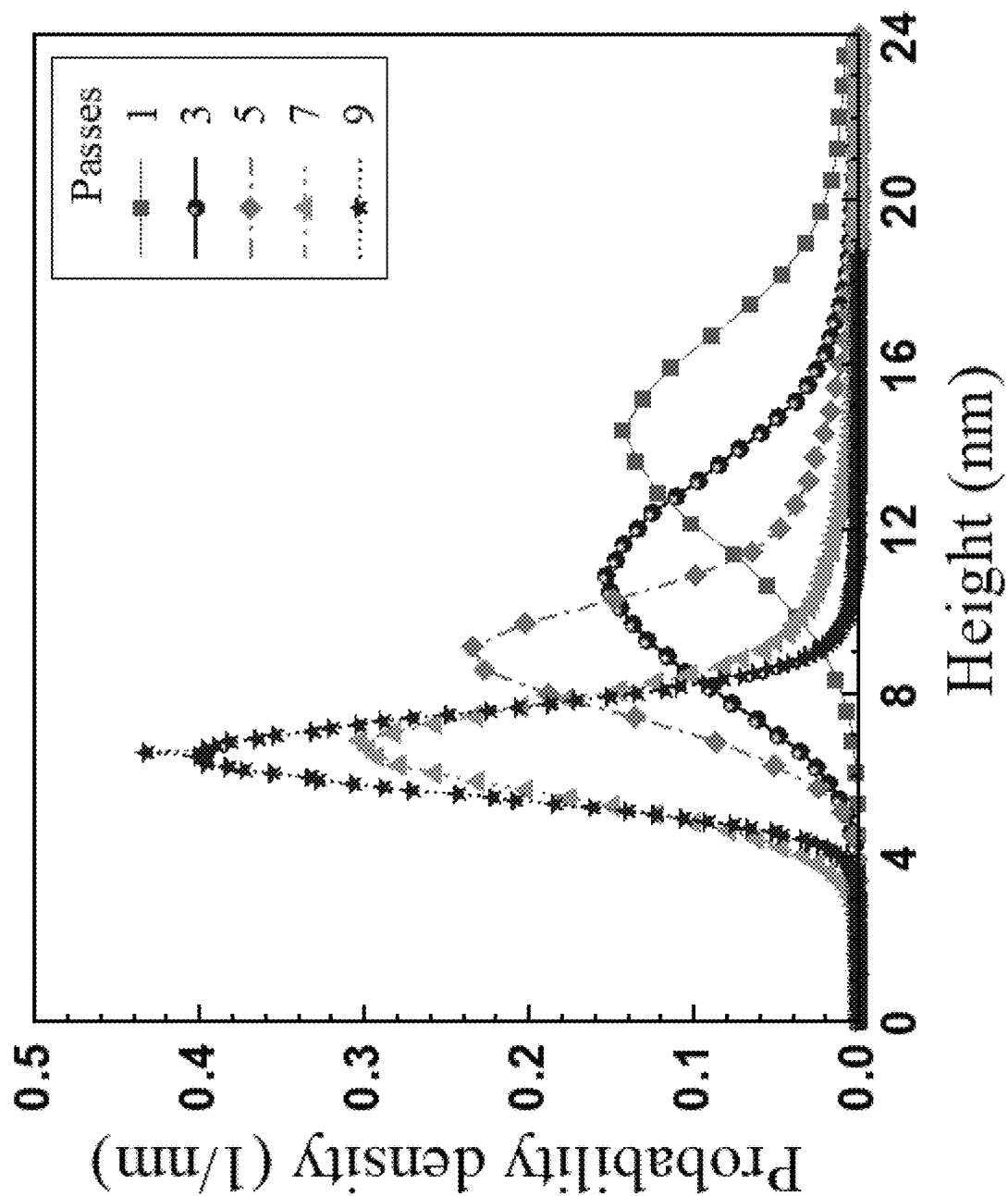
FIG. 9. The extent of mechanical fibrillation on fibril height distribution probability density of LCNFs from birch WIS under M50T100t30 by AFM topographical measurements.
Figures 10E, 10F:
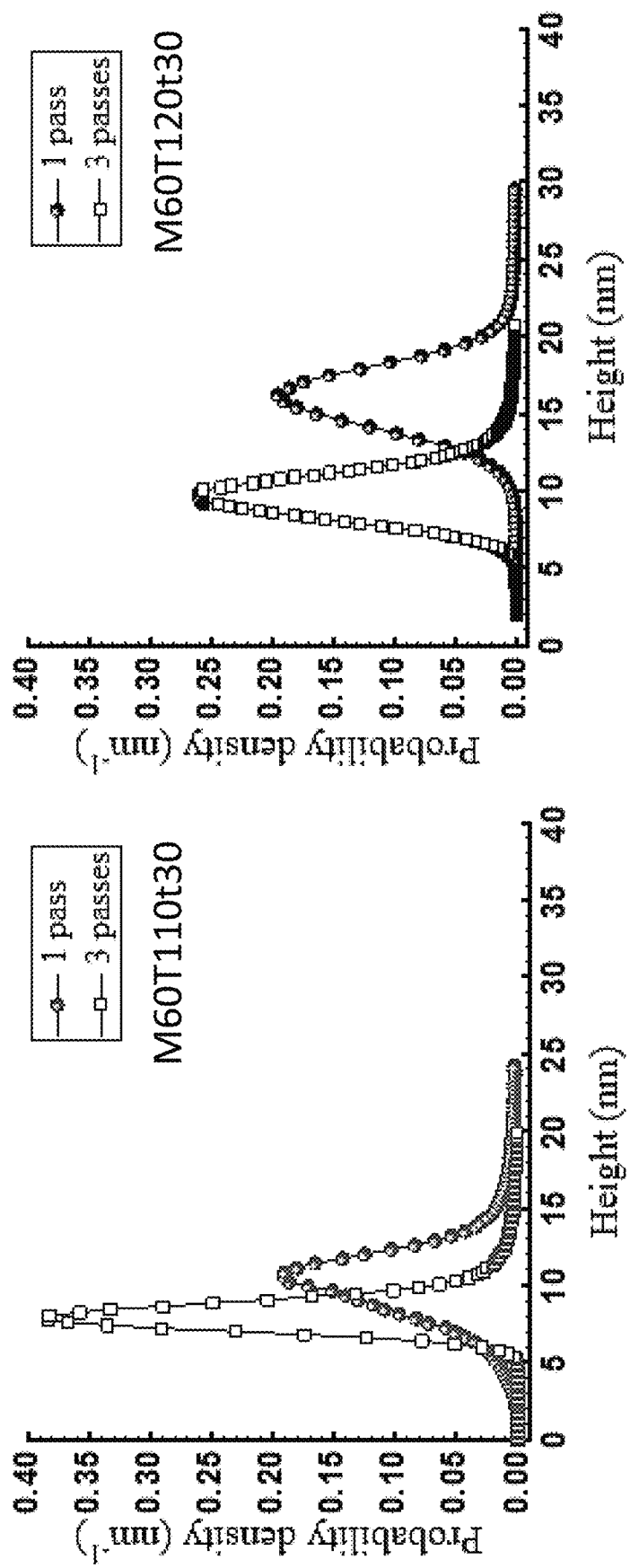

Because maleic acid is a weak acid, the amount of lignin-containing cellulose nanocrystals (LCNCs) produced by concentrated maleic acid hydrolysis of lignocelluloses is very low under most fractionation conditions as demonstrated previously (Bian et al., 2017a). In this example, LCNCs were not separated. The WIS from maleic acid fractionation were directly mechanically-fibrillated to produce lignin-containing cellulose nanofibrils (LCNFs) or lignin-containing microfibrils (LCMFs), depending on the extent of fibrillation and the severity of fractionation. The WIS suspensions were diluted with water to 0.5% and fibrillated using a microfluidizer (M-110EH, Microfluidics Corp., Westwood, Ma.). The suspensions were initially processed through a 200 μm chamber 5 times at 40 MPa, and then passed through an 87 μm chamber at 120 MPa for 5 additional passes. Gelation was observed, suggesting that the solid suspensions became nanofibrils. Atomic Force Microscopy (AFM) images confirmed this, as shown in FIGS. 6A-6D. These samples were produced using WIS from M60T90t30, M50T100t30, M50T100t60, and M70T100t15, respectively, with 5 passes through the microfluidizer. AFM-measured fibril height probability density distributions from these four samples are shown in FIG. 7, with peak height of approximately 12, 9, 7, 6 nm, respectively. The fibrillation through the 87 μm chamber substantially reduced the fibril height (diameter) with small variation among samples, except for the sample from the low temperature (90° C.) and fractionation of M60T90t30. The results in FIG. 7 indicate that increasing fractionation severity by using a longer reaction time or a high temperature reduced the fibril height (diameter) and improved distribution uniformity.

The effect of the extent of fibrillation on the morphology of the LCNFs can be seen from FIGS. 8A-8D. Even with one pass through the 87 μm chamber at 120 MPa, the WIS from M50T10030 was fibrillated to fairly fine and uniform LCNFs. Increasing the passes through the 87 μm chamber reduced the diameter (height), reduced entanglement, and improved the uniformity of the fibrils, as shown in FIGS. 8A-8D and FIG. 9. The mean LCNF height was respectively reduced from 14.4 to, 10.8, 9.1, 6.9, 6.6 nm after increasing the numbers of passes through the 87 μm chamber of the microfluidizer from 1 to, 3, 5, 7, and 9. Comparing with p-TsOH fractionation (Bian et al., 2017b), it appears that maleic acid fractionation substantially facilitated fibrillation for samples with a similar degree of delignification and hemicellulose removal.

The effect of fractionation severity and the extent of fibrillation can also be seen from FIGS. 10A-10F (≤110° C.). At seventies higher than those reported in FIGS. 6A-6D (≤100° C.), one pass through microfludization can result in fine nanofibrils.

Maleic acid hydrolysis esterified cellulose and lignin to result in highly charged LCNFs, as listed in Table 4. The carboxyl group contents were around 0.1-0.2 mmol/g for the conditions tested. Increasing hydrolysis time and acid concentration increased esterification and surface charge. However, the effect of temperature on esterification and the surface charge of the resultant LCNFs was more pronounced and played a more significant role in esterification. The surface charge provided LCNF good dispersity, as can be seen from the AFM images shown in FIGS. 6A-6D and FIGS. 10A-10F.

TABLE 4

Measured carboxyl group contents and zeta-potential of LCNFs at pH = 7.0.

| LCNF sample | COOH group (mmol/g) | Charge (mV) |
| --- | --- | --- |
| M50T100t15-5P | 0.105 ± 0.012 | −43.4 ± 0.8 |
| M50T100t30-5P | 0.134 ± 0.009 | −46.3 ± 1.4 |
| M70T100t15-5P | 0.122 ± 0.013 | −44.1 ± 0.9 |
| M60T90t30-5P | 0.084 ± 0.008 | −41.4 ± 1.9 |
| M60T110t30-3P | 0.218 ± 0.009 | −40.8 ± 2.5 |
| M60T120t30-3P | 0.216 ± 0.008 | −42.3 ± 3.3 |

Example 6: Production of Lignin Nanoparticles from Spent Liquor

Figure 11:
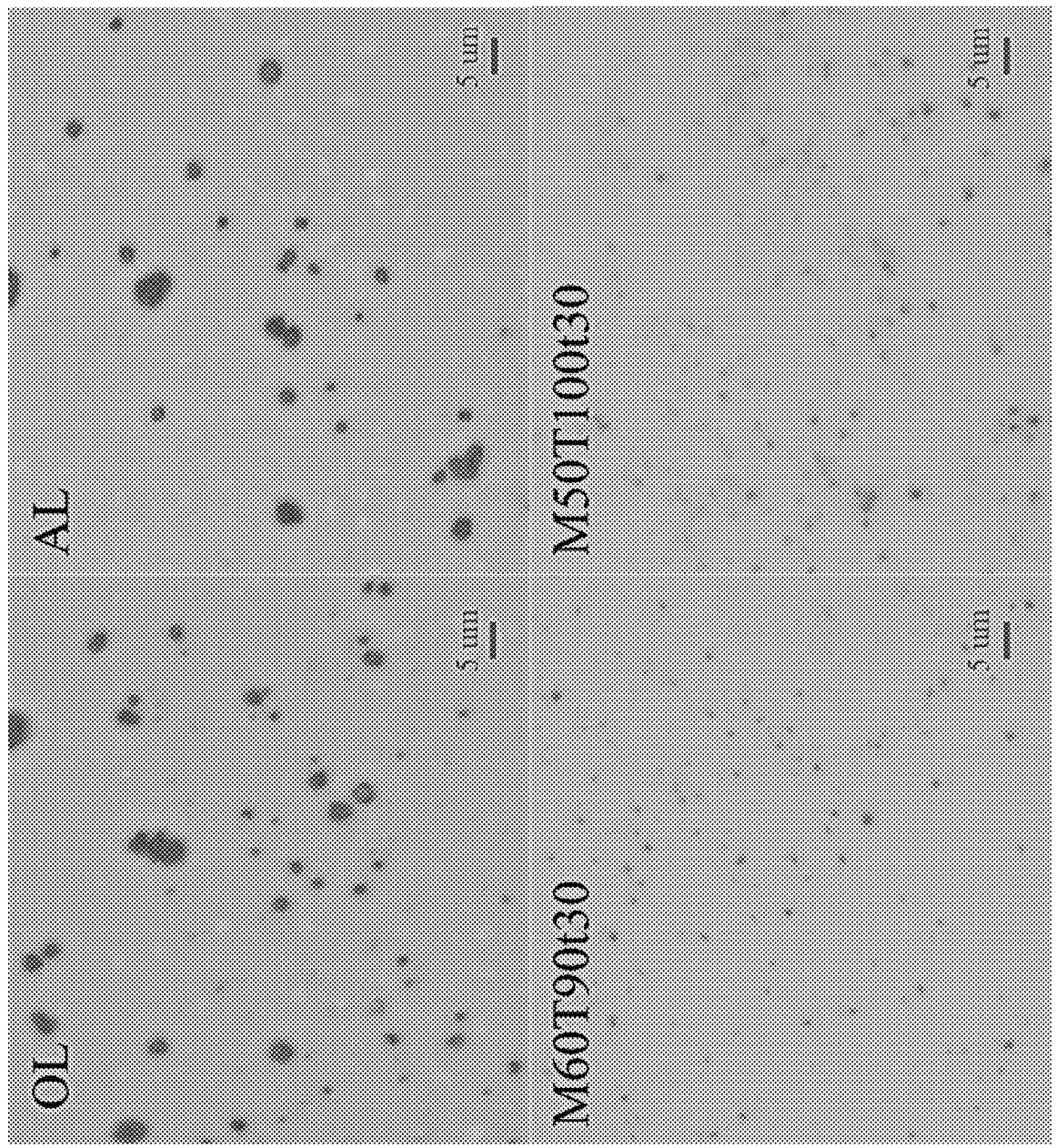
FIG. 11. Comparisons of lignin nanoparticles (LNPs) from maleic acid fractionation under two sets of conditions with lignin particles from organosolv (OL) and alkaline (AL) fractionations.

The dissolved lignin can be precipitated as lignin nanoparticles. At the minimal hydrotrope concentration (MHC), hydrotropy is exhibited, i.e., below MHC lignin solubility disappears. As discussed in Example 3, the MHC for maleic acid is approximately 25 wt. %. Therefore, when the spent liquor was diluted below 25 wt. %, self-association disappeared. The solubility of lignin in the solution was impaired, resulting in precipitation. The precipitated lignin was freeze dried. The dried lignin was re-suspended in water at 1 g/L and sonicated. The sonicated suspension was observed under an optical microscope after a dilution of 10 times. The results were compared with organosolv and alkali lignin aqueous suspensions prepared under the same condition, as shown in FIG. 11. The results indicate that the lignin from maleic acid fractionation is much more dispersible in water with particle size in the hundreds of nanometers range or lower.

over 63%, when compared to M50T100t120, which had a lower severity of CDF=603 but a much longer fractionation time of 120 min (Table 5, FIG. 12), suggesting prolonged reaction time should be avoided to reduce lignin condensation.

TABLE 5

$^{13}$C-$^1$H 2D NMR HSQC spectral analyses of side chains and aromatic units present in AHLs from batch maleic acid fractionations of birch.

| Run labels | CDF | $S_{2/6}$ | $S'_{2/6}$ | $S_{conden}$ | S | G | S/G | β-O-4 (%) | β-5 (%) | β-β (%) | AHL yield (%) |
|---|---|---|---|---|---|---|---|---|---|---|---|
| MWL |  | 76.7 | 4.1 |  | 80.8 | 19.2 | 4.2 | 64.6 | 1.2 | 11.2 |  |
| M50T80t60 | 18 | 77.2 | 2.7 | 2.9 | 82.8 | 17.2 | 4.8 | 64.5 | 0.7 | 8.0 | 24.6 |
| M50T80t6OR [a] | 18 | 70.6 | 2.4 | 8.8 | 81.8 | 18.2 | 4.5 | 66.0 | 0.6 | 7.3 |  |
| M50T80t6OR' [a] | 18 | 77.5 | 2.7 | 2.3 | 82.5 | 17.5 | 4.7 | 65.1 | 0.8 | 8.5 |  |
| M50T90t60 | 77 | 79.7 | 2.8 | 1.9 | 84.4 | 15.6 | 5.4 | 67.3 | 0.8 | 8.8 | 38.1 |
| M50T100t30 | 151 | 75.6 | 2.5 | 9.3 | 87.3 | 12.7 | 6.9 | 54.1 | 0.2 | 7.8 | 48.9 |
| M50T100t60 | 302 | 64.4 | 3.9 | 21.4 | 89.7 | 10.3 | 8.7 | 27.1 | 7.0 | 0.8 | 50.3 |
| M50T100t120 | 603 | 56.4 | 4.1 | 32.6 | 93.2 | 6.8 | 13.6 | 16.1 | 0.1 | 4.9 | 56.3 |
| M70T80t60 | 443 | 71.7 | 2.8 | 14.6 | 89.0 | 11.0 | 8.1 | 43.3 | 0.5 | 7.2 | 46.2 |
| M60T90t30 | 185 | 66.1 | 2.5 | 15.7 | 84.3 | 15.7 | 6.4 | 52.8 | 1.0 | 7.9 | 48.1 |
| M60T110t30 | 547 | 74.0 | 3.3 | 9.8 | 87.1 | 12.9 | 6.7 | 41.0 | 1.0 | 11.1 | 47.7 |
| M60T120t30 | 1857 | 62.9 | 3.2 | 25.4 | 91.5 | 8.5 | 10.7 | 26.7 | 0.1 | 8.9 | 63.4 |

[a] R and R' stand for replicate fractionation runs

Example 7: Chemical Structure of AHL from Birch by $^{13}$C-$^1$H 2D NMR

2D $^{13}$C-$^1$H NMR HSQC spectral analyses of side chains and aromatic units present in the dissolved AHLs from batch maleic acid fractionations of birch are listed in Table 5. The results indicate that a large amount of β-O-4 ether linkages in the dissolved AHL can be preserved under mild conditions, such as T≤100° C. for ≤30 min at maleic acid concentration of 50 wt. %, corresponding to a CDF≤150. The condensed units, $S_{conden}$, constitute less than 10%. As expected, the lignin remaining on the washed cellulosic solid fraction was even less condensed than the dissolved AHL for batch operations. Lignin with a low degree of condensation tends to have a low glass transition temperature (Cheng et al., 2019), beneficial for lignin valorization through compounding. Low lignin condensation is beneficial for lignin valorization either as a polymer or for further depolymerizing into monomers.

Figure 12:
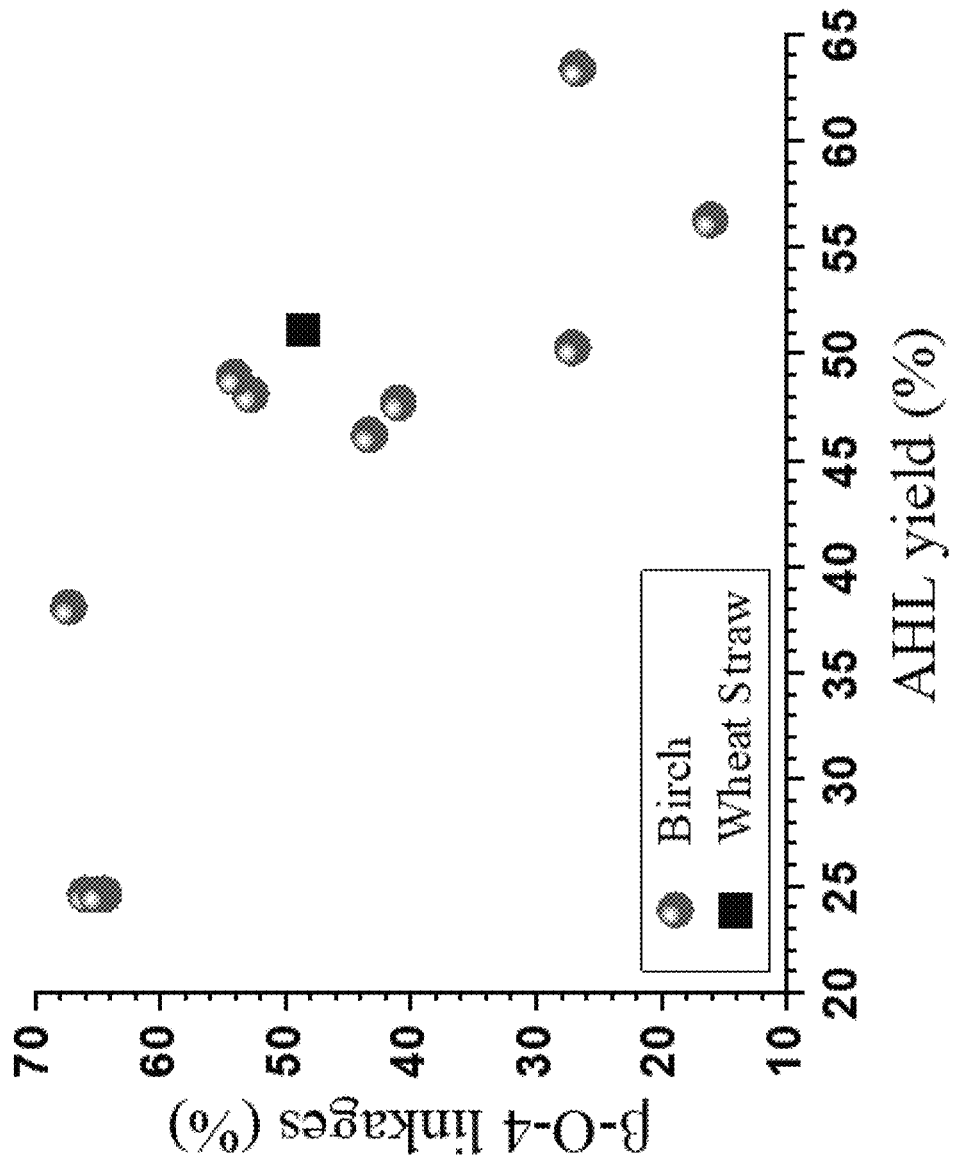
FIG. 12. A correlation between lignin dissolution (yield) by maleic acid hydrotropic fractionation and extent of lignin reactivity represented by retained β-O-4 linkages in the dissolved acid hydrotropic lignin (AHL).

Because lignin yield is also important, FIG. 12 shows the correlation between AHL yield and the content of β-O-4 ether linkages measured from 2D $^{13}$C-$^1$H NMR. The results indicate that approximately 80% of the original β-O-4 can be retained even at an AHL yield of over 45%, which is near the limit of maleic acid delignification of 55% achieved at acid concentration of 50% (Table 1), The AHL from M60T120t30 had a substantially greater amount of β-O-4 linkages, despite having a much higher severity of CDF=1857 and having a greater degree of delignification of

Example 8: Molecular Weight Distribution of Birch AHL

Figure 13:
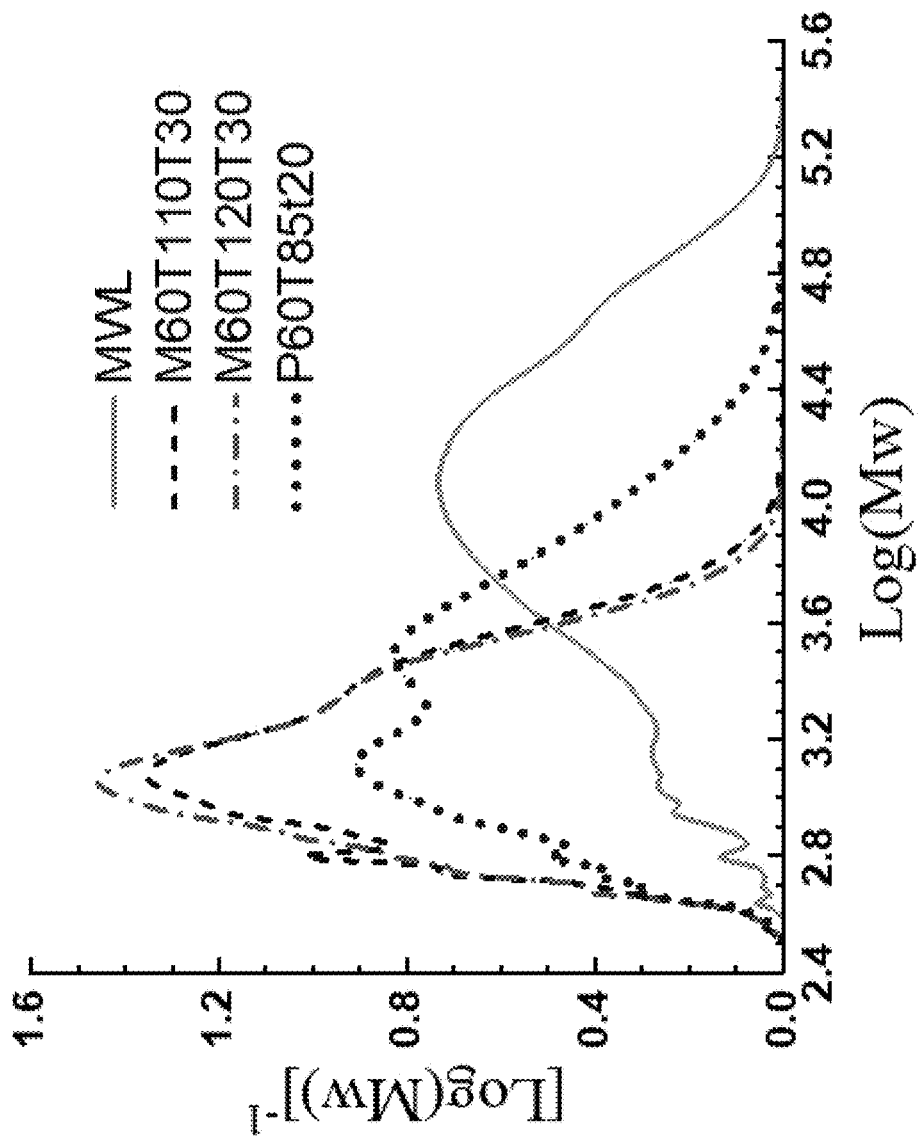
FIG. 13. Molecular weight distributions of the birch wood AHLs under different fractionation conditions in comparison with that of milled wood lignin (MWL).

The weight-average molecular weight (Mw) and number-average molecular weight (Mn) of birch MWL are 3227 and 14832, respectively, with a broad distribution as shown in FIG. 13. AHF substantially depolymerized lignin as well as repolymerized lignin through forming C—C bonds to condense lignin. Both AHLs shown have much lower molecular weight and more narrow (or more uniform) distribution than MWL because of increased depolymerization (FIG. 13). The fact that the Mw distribution of AHL from M60T120t30 almost completely overlaps the AHL from M60T110t30, with only a slight decrease in average Mw, suggests that repolymerization starts becoming important as fractionation temperature increases above 110° C. and approaches the boiling point of approximately 130° C. This is also reflected in the decrease in β-O-4 linkages (Table 5).

Example 9: Maleic Acid Fractionation of Wheat Straw

Lightly hammer-milled wheat straw was fractionated directly using concentrated maleic acid solution in a wide range of conditions. The wheat straw was first water washed to remove dirt. Good selectivity in dissolving lignin over cellulose was obtained, as listed in Table 6. At a relatively low maleic acid concentration of 40 wt. %, over 50% of the straw lignin was dissolved while over 85% of cellulose was retained. The wheat straw also contained a small amount of silicate, as can be seen from the ash content of 0.9% listed in Table 6 (obtained by burning at 560° C. the residual solids after a two-step sulfuric acid hydrolysis of carbohydrates). It appears that silicate was fully retained in the WIS after maleic acid fractionation. This is beneficial, as it helps to increase the WIS yield for material production as well as avoiding silicate-caused equipment corrosion problems in downstream processing. The silicate can also improve the hydrophobicity of the solids for LCNF or LCMF production.

TABLE 6

Chemical compositions of maleic acid fractionation of wheat straw samples under different conditions. The numbers in the parentheses are component yields based on the component in the untreated wheat straw.

| Sample Label [1] | Solids yield (%) | Glucan (%) | Xylan (%) | Ash (%) | K. Lignin (%) |
|---|---|---|---|---|---|
| Untreated Wheat Straw | 100 | 37.9 | 21.2 | 0.9 | 22.3 |
| M20T60t30Ws | 87.0 | 37.0 (85.1) | 19.3 (79.1) | 1.2 (108) | 21.4 (83.7) |
| M20T60t60Ws | 86.7 | 37.9 (86.6) | 19.1 (78.5) | 1.3 (115) | 21.1 (82.1) |
| M20T60t90Ws | 86.9 | 37.4 (85.9) | 19.0 (77.9) | 1.2 (106) | 22.1 (86.1) |
| M20T70t30Ws | 86.9 | 35.6 (81.7) | 19.5 (80.1) | 0.8 (76) | 20.8 (81.1) |
| M40T80t30Ws | 80.9 | 40.7 (87.0) | 16.9 (64.4) | 1.4 (120) | 20.2 (73.4) |
| M40T80t60Ws | 72.5 | 42.9 (82.2) | 15.2 (52.1) | 1.4 (108) | 20.1 (65.3) |
| M40T80t90Ws | 67.3 | 45.2 (80.3) | 13.7 (43.6) | 1.5 (104) | 19.9 (60.2) |
| M40T80t120Ws | 62.0 | 44.6 (73.0) | 11.8 (34.4) | 1.2 (77) | 22.4 (62.2) |
| M50T90t90Ws | 68.5 | 48.8 (88.4) | 11.0 (35.5) |  | 16.2 (49.8) |
| M60T100t30Ws | 64.5 | 54.2 (92.4) | 10.8 (32.9) | 1.6 (108) | 16.0 (46.4) |
| M60T100t60Ws | 54.6 | 53.7 (77.5) | 9.5 (24.5) | 1.2 (69) | 16.4 (40.2) |
| M60T100t90Ws | 57.1 | 53.0 (79.9) | 8.3 (22.4) | 1.3 (77) | 16.3 (41.7) |
| M60T110t30Ws | 60.7 | 49.0 (78.6) | 10.0 (28.7) | 1.6 (103) | 17.1 (46.7) |
| M60T110t60Ws | 53.1 | 56.9 (79.8) | 9.4 (23.6) | 1.7 (98) | 14.1 (33.5) |
| M60T110t90Ws | 53.9 | 56.8 (80.9) | 5.8 (14.7) | 1.6 (89) | 17.1 (41.5) |
| M60T120t30Ws | 58.8 | 48.3 (75.0) | 7.2 (19.9) | 1.4 (87) | 17.1 (45.2) |
| M60T120t60Ws | 58.8 | 56.4 (87.7) | 8.4 (23.3) | 1.9 (116) | 16.4 (43.4) |
| M60T120t90Ws | 47.5 | 33.7 (42.3) | 3.0 (6.7) | 1.0 (48) | 13.5 (28.8) |
| M60T120t120Ws | 51.4 | 17.1 (23.2) | 0.8 (2.0) | 0.3 (14) | 4.4 (10.1) |

[1] (Mxx, Txx, txx) stands for maleic acid concentration in wt. %, reaction temperature in ° C. and reaction duration in min.

Figure 14A:
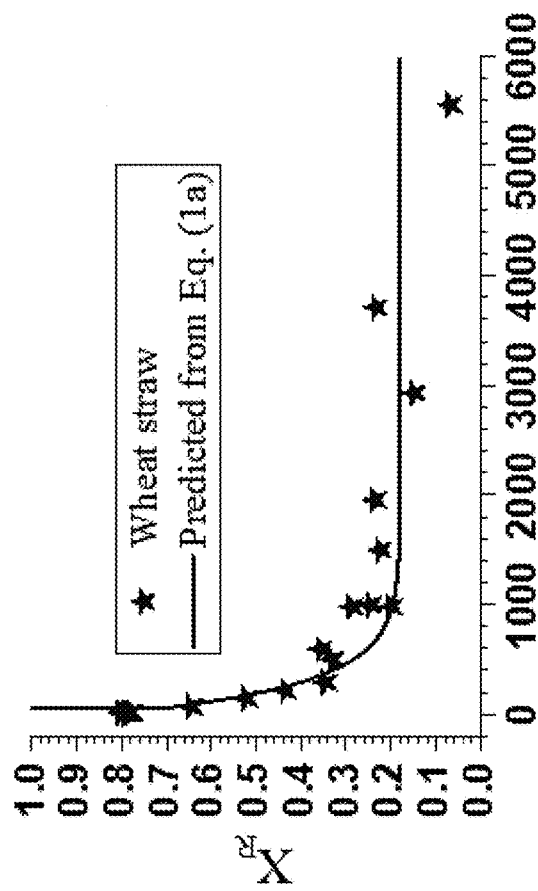
FIGS. 14A-14B. Experimentally measured wheat straw xylan (FIG. 14A) and lignin (FIG. 14B) dissolutions by maleic acid fractionation under different conditions along with their predictions based on reaction-severity-based reaction kinetics.
Figure 14B:
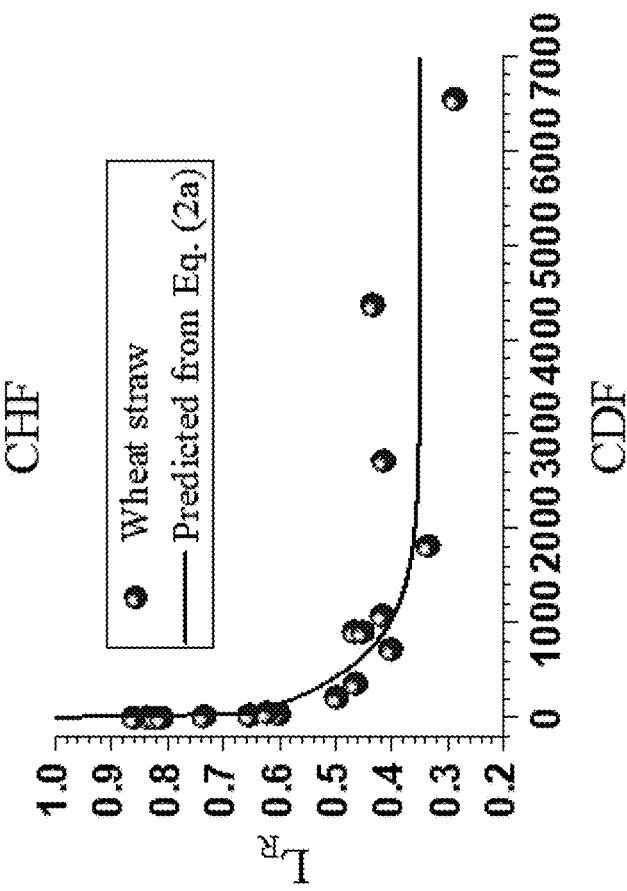

Delignification and hemicellulose dissolution by maleic acid can also be fitted to Eqs. (1) and (2) using reaction severity factors, CHF and CDF as shown in FIGS. 14A-14B. The fitting parameters are listed in Table 7. The results indicate that wheat straw xylan dissolution is independent of maleic acid concentration as $\beta=0$.

TABLE 7

Fitting parameters in Eqs. (1) and (2) from wheat straw xylan and lignin yield data listed in Table 6.

| Parameter | Unit | Xylan | Lignin |
|---|---|---|---|
| α, α' | None | 27.20 | 34.31 |
| β, β' | L/mol | 0 | 0.55 |
| E, E' | J/mol | 80,000 | 110,000 |
| θ, θ' | None | 0.639 | 0.320 |
| f, f' | None | 0.0037 | 0.0018 |
| $\theta_R, \theta'_R$ | None | 0.18 | 0.35 |

Example 10: Maleic Acid Fractionation of Switchgrass

As another example, maleic acid fractionation was also applied to switchgrass. The switchgrass was Wiley-milled with a 1-cm mesh size screen. The materials that passed the screen were used. Switchgrass fractionation experiments using MA solutions were carried out at a solid to acid solution ratio of 1:15 (w/w) under a range of acid concentration, temperature and reaction time duration. Again, fractionation runs were labeled as MxxTyytzz to represent MA concentration of xx wt. % at yy ° C. for zz min as listed in Table 8.

TABLE 8

Chemical compositions of maleic acid fractionation of switchgrass samples under different conditions. The numbers in the parentheses are component yields based on the component in the untreated wheat straw.

| Sample Label [1] | Solids yield (%) | Glucan (%) | Xylan (%) | Ash (%) | K. Lignin (%) |
|---|---|---|---|---|---|
| Untreated Wheat Straw | 100 | 35.7 | 20.5 | 2.0 | 25.1 |
| M20T60t30Sg | 98.5 | 34.8 (90.6) | 22.3 (79.1) | 2.2 (109) | 25.5 (83.7) |
| M20T60t60Sg | 96.7 | 34.7 (88.5) | 25.7 (78.5) | 2.5 (115) | 21.9 (82.1) |
| M20T80t90Sg | 85.4 | 41.5 (93.6) | 17.5 (77.9) | 2.2 (106) | 26.5 (86.1) |
| M30T70t30Sg | 95.0 | 35.8 (89.9) | 23.1 (104) | 2.3 (236) | 24.6 (101) |
| M30T70t60Sg | 91.6 | 36.1 (87.2) | 22.4 (96.8) | 2.2 (212) | 24.5 (95.8) |
| M30T70t90Sg | 86.4 | 38.5 (87.9) | 21.7 (88.4) | 2.0 (183) | 24.7 (86.9) |
| M40T80t60Sg | 79.8 | 41.4 (87.3) | 17.8 (67.3) | 2.4 (208) | 24.3 (77.1) |
| M40T90t120Sg | 59.7 | 49.4 (77.9) | 12.1 (34.0) | 3.1 (198) | 24.2 (64.8) |

TABLE 8-continued

Chemical compositions of maleic acid fractionation of switchgrass samples under different conditions. The numbers in the parentheses are component yields based on the component in the untreated wheat straw.

| Sample Label [1] | Solids yield (%) | Glucan (%) | Xylan (%) | Ash (%) | K. Lignin (%) |
|---|---|---|---|---|---|
| M50T90t30Sg | 74.9 | 41.7 (82.5) | 15.4 (54.5) | 2.6 (206) | 23.8 (80.0) |
| M50T90t60Sg | 61.1 | 50.4 (81.4) | 14.6 (42.1) | 2.9 (189) | 20.2 (55.4) |
| M50T90t90Sg | 58.3 | 48.7 (75.1) | 11.9 (32.8) | 3.49 (216) | 22.2 (58.2) |
| M50T100t60Sg | 62.2 | 48.1 (79.0) | 12.2 (36.0) | 2.89 (191) | 21.3 (59.4) |
| M50T110t60Sg | 57.8 | 52.4 (80.0) | 11.5 (31.4) | 3.07 (188) | 18.9 (48.9) |
| M60T100t60Sg | 58.5 | 53.7 (82.9) | 12.3 (34.0) | 2.79 (173) | 18.2 (47.8) |
| M60T110t30Sg | 60.5 | 52.4 (83.7) | 12.5 (35.6) | 2.59 (166) | 18.1 (49.1) |
| M60T110t60Sg | 51.5 | 59.4 (80.9) | 11.1 (27.0) | 3.25 (178) | 12.6 (29.1) |
| M60T110t90Sg | 49.8 | 59.0 (77.6) | 9.5 (22.3) | 3.53 (187) | 16.5 (36.8) |
| M60T120t30Sg | 54.7 | 56.0 (81.0) | 8.1 (21.0) | 3.35 (195) | 17.2 (42.2) |
| M60T120t90Sg | 58.9 | 51.6 (80.3) | 6.3 (17.6) | 3.52 (221) | 15.5 (41.0) |

[1] (Mxx, Txx, txx) stands for maleic acid concentration in wt. %, reaction temperature in ° C. and reaction duration in min.

Figure 15A:
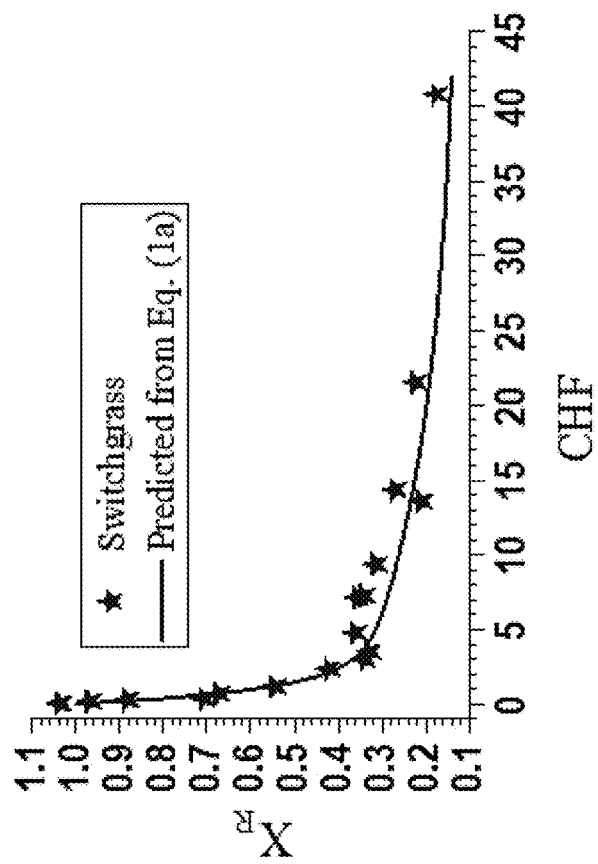
FIGS. 15A-15B. Experimentally measured switchgrass xylan (FIG. 15A) and lignin (FIG. 15B) dissolutions by maleic acid fractionation under different conditions along with their predictions based on reaction-severity-based reaction kinetics.
Figure 15B:
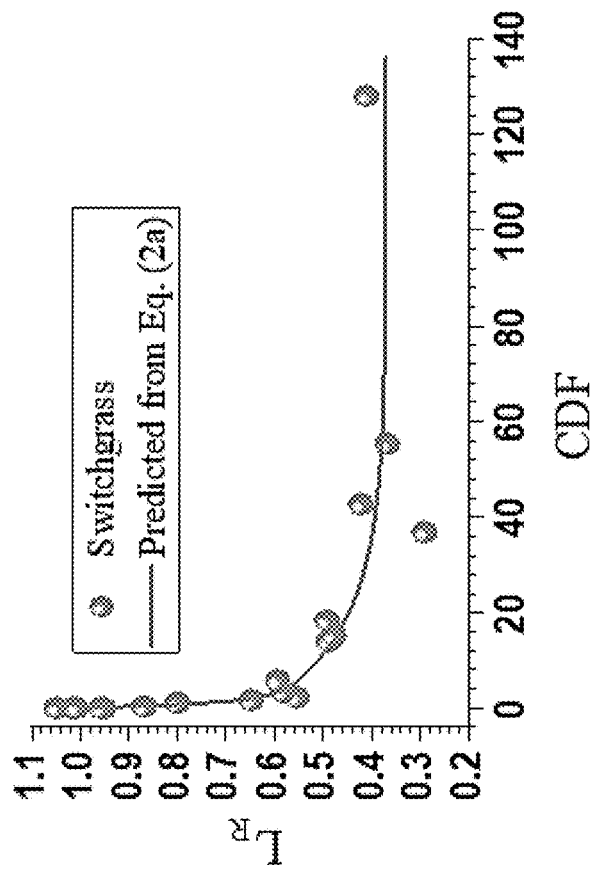

Again, dissolutions of lignin and xylan by maleic acid hydrotropic fractionation can be fitted to Eqs. (1) and (2) using reaction severity factors, CHF and CDF as shown in FIGS. 15A-15B. The fitting parameters are listed in Table 9. The large difference between $\beta$ and $\beta'$ results indicate that delignification has a stronger dependence on acid concentration than does xylan dissolution.

TABLE 9

Fitting parameters in Eqs. (1) and (2) from switchgrass xylan and lignin yield data listed in Table 8.

| Parameter | Unit | Xylan | Lignin |
|---|---|---|---|
| $\alpha, \alpha'$ | None | 21.20 | 27.16 |
| $\beta, \beta'$ | L/mol | 0.267 | 0.965 |
| E, E' | J/mol | 80,000 | 105,000 |
| $\theta, \theta'$ | None | 0.256 | 0.254 |
| f, f' | None | 0.0408 | 0.0594 |
| $\theta_R, \theta'_R$ | None | 0.12 | 0.37 |

Example 11: Chemical Structure of AHLs from Wheat Straw and Switchgrass

The chemical structure of AHLs from wheat straw and switchgrass dissolved by maleic acid were analyzed by $^{13}C$-$^{1}H$ 2D NMR. As shown in Table 10, the AHLs from different fractionation conditions have high $\beta$-O-4 linkage contents, suggesting a low degree of condensation. Increasing fraction severity resulted in decreased $\beta$-O-4 linkage content, as expected. Under same level of delignification, the AHL from switchgrass had relatively higher $\beta$-O-4 than wheat straw. For example, under approximately 57% delignification for both substrates, approximately 54% of the $\beta$-O-4 was lost (based on wheat straw MWL) vs. a loss of 39% for switchgrass. This is perhaps because it is relatively easier to delignify switchgrass with a shorter reaction time of 30 min than with the 60 min needed for wheat straw to achieve equivalent delignification. Lignin esterification was also increased with the increase in fractionation severity. Grass materials such as straw and switchgrass naturally contain esterified lignin, as can be seen from the MWL of wheat straw and switchgrass in Table 10.

TABLE 10

Amount of lignin substructure and LCCs linkages along with mean molecular weight of MWL and AHL samples.

| | MWL-Ws | Fractionation Lignin removal (%) | | | MWL-Sg |
|---|---|---|---|---|---|
| | | M40T80t120W 37.8 | M60T100t30W 53.6 | M60120t60W 56.6 | |
| Lignin samples | Ws-MWL | WsL-T80 | WsL-T100 | WsL-T120 | Sg-MWL |
| Mw | 13157 | 8096 | 7009 | 5047 | 13091 |
| Mn | 4461 | 3645 | 3708 | 3157 | 4803 |
| Mw/Mn | 2.9 | 2.2 | 1.9 | 1.6 | 2.7 |
| Interunit linkages [a] | | | | | |
| $\beta$-O-4' (A) | 53.6 | 50.3 | 38.1 | 25.1 | 47.1 |
| $\beta$-5' (B) | 6.2 | 3.4 | 5.9 | 6.3 | 5.9 |
| $\beta$-$\beta$' (C) | 7.0 | 7.9 | 9.6 | 10.2 | 6.1 |
| Condensed degree[c] | 19.8 | 18.3 | 28.9 | 39.7 | 20.3 |
| $\gamma$-esterification | 12.2 | 14.7 | 26.8 | 37.2 | 6.8 |
| HK$\alpha$ | ND | ND | 2.4 | 7.7 | ND |
| Aromatic units[b] | | | | | |
| S | 39 | 50 | 53 | 59 | 32 |
| $S_{cond}$ | ND | 1 | 5 | 9 | ND |
| G | 58 | 47 | 44 | 38 | 65 |
| H | 3 | 3 | 3 | 3 | 3 |
| S/G ratio | 0.67 | 1.11 | 1.2 | 1.55 | 0.49 |

TABLE 10-continued

Amount of lignin substructure and LCCs linkages along with mean molecular weight of MWL and AHL samples.

| p-Hydroxycinnamates[b] | | | | | |
|---|---|---|---|---|---|
| p-coumarates | 6.8 | 3.3 | 4.3 | 2.9 | 15.8 |
| ferulates | 2.0 | 2.8 | 0.9 | 0.7 | 4.0 |
| Flavonoid[b]: Tricin | 9.6 | 2.7 | 1.0 | 0.9 | 4.2 |
| LCC linkages | | | | | |
| PhGlc | 6.0 | 3.3 | 2.2 | 1.8 | 3.9 |
| BE | 7.3 | 3.4 | 1.5 | 1.6 | 3.1 |

Fractionation Lignin removal (%)

| | M30T70t90S | M40T90t120S | M50T90t90S | M60T100t60S | M60T120t30S |
|---|---|---|---|---|---|
| | 13.1 | 35.2 | 41.8 | 52.2 | 57.8 |
| Lignin samples | SgL-T70 | SgL-T90 | SgL-T9OH | SgL-T100 | SgL-T120 |
| Mw | 8458 | 7464 | 7009 | 6520 | 4841 |
| Mn | 3666 | 3922 | 3708 | 3817 | 3067 |
| Mw/Mn | 2.3 | 1.9 | 1.9 | 1.7 | 1.6 |
| Interunit linkages [a] | | | | | |
| β-O-4' (A) | 46.9 | 41.2 | 37.8 | 33.3 | 28.8 |
| β-5' (B) | 3.3 | 3.5 | 4.0 | 4.8 | 5.2 |
| β-β' (C) | 1.4 | 2.0 | 1.5 | 1.7 | 1.9 |
| Condensed degree[c] | 9.1 | 10.5 | 12.7 | 16.3 | 19.8 |
| γ-esterification | 15.3 | 17.7 | 33.5 | 40.6 | 46.8 |
| HKα | ND | 1.7 | 0.8 | 2.3 | 3.7 |
| Aromatic units[b] | | | | | |
| S | 30 | 34 | 36 | 36 | 38 |
| Scond | 1 | 2 | 2 | 3 | 4 |
| G | 66 | 63 | 60 | 61 | 57 |
| H | 4 | 3 | 4 | 4 | 5 |
| S/G ratio | 0.45 | 0.54 | 0.60 | 0.59 | 0.67 |
| p-Hydroxycinnamates[b] | | | | | |
| p-coumarates | 16.6 | 14.8 | 17.1 | 18.0 | 18.3 |
| ferulates | 1.3 | 1.5 | 1.8 | 2.0 | 1.7 |
| Flavonoid[b]: Tricin | 0.6 | 0.4 | 0.4 | 0.5 | 0.4 |
| LCC linkages | | | | | |
| PhGlc | 1.5 | 1.7 | 1.5 | 1.5 | 1.5 |
| BE | 1.6 | 1.2 | 1.1 | 1.2 | 1.1 |

[a] Molar percentages (H + G + S = 100).
[b] Interunit linkages, p-coumarate, ferulate and tricin molar contents as percentages of lignin content (H + G + S).
[c] Condensed degree, % = 100 * $(I_{B\alpha} + I_{C\alpha})/(I_A + I_{B\alpha} + I_{C\alpha})$, where I refers to the integral value of each signal in 2D HSQC NMR.

Example 12: Enzymatic Sugar Production from Maleic Acid Fractionated Wheat Straw and Switchgrass Cellulosic Solids The MA fractionated wheat straw and switchgrass WISs are both highly enzymatically digestible for sugar production. However, under similar levels of delignification and xylan dissolution, the switchgrass WISs were more digestible than wheat straw WIS (Table 11). This is due to the differences between these two raw materials. Table 12 shows that the residual switchgrass lignin on LCNFs derived from fractionated WISs were more esterified (carboxylated) than those of wheat straw. As a result, less cellulase was non-productively bonded to the lignin in the switchgrass WISs than the amount bonded to lignin in the corresponding wheat straw WIS, when enzymatic hydrolysis was conducted at elevated pH of 6.0.

TABLE 11

Comparisons of substrate enzymatic digestibility (SED) between fractionated wheat straw and switchgrass WISs with similar delignification and xylan dissolution. Cellulase CTec3 loading was 10 FPU/glucan for all samples.

| WIS Sample | Lignin content (removal) (%) | Xylan content (removal) (%) | SED @ 96 h (%) |
|---|---|---|---|
| M40T80t120Ws | 22.4 (37.8) | 11.8 (65.6) | 41.6 |
| M40T90t120Sg | 24.2 (35.2) | 12.1 (66.0) | 45.4 |
| M60T100t30Ws | 16.0 (53.6) | 10.8 (67.1) | 60.9 |
| M60T100t60Sg | 18.2 (53.2) | 12.3 (66.0) | 73.1 |

Figure 17:
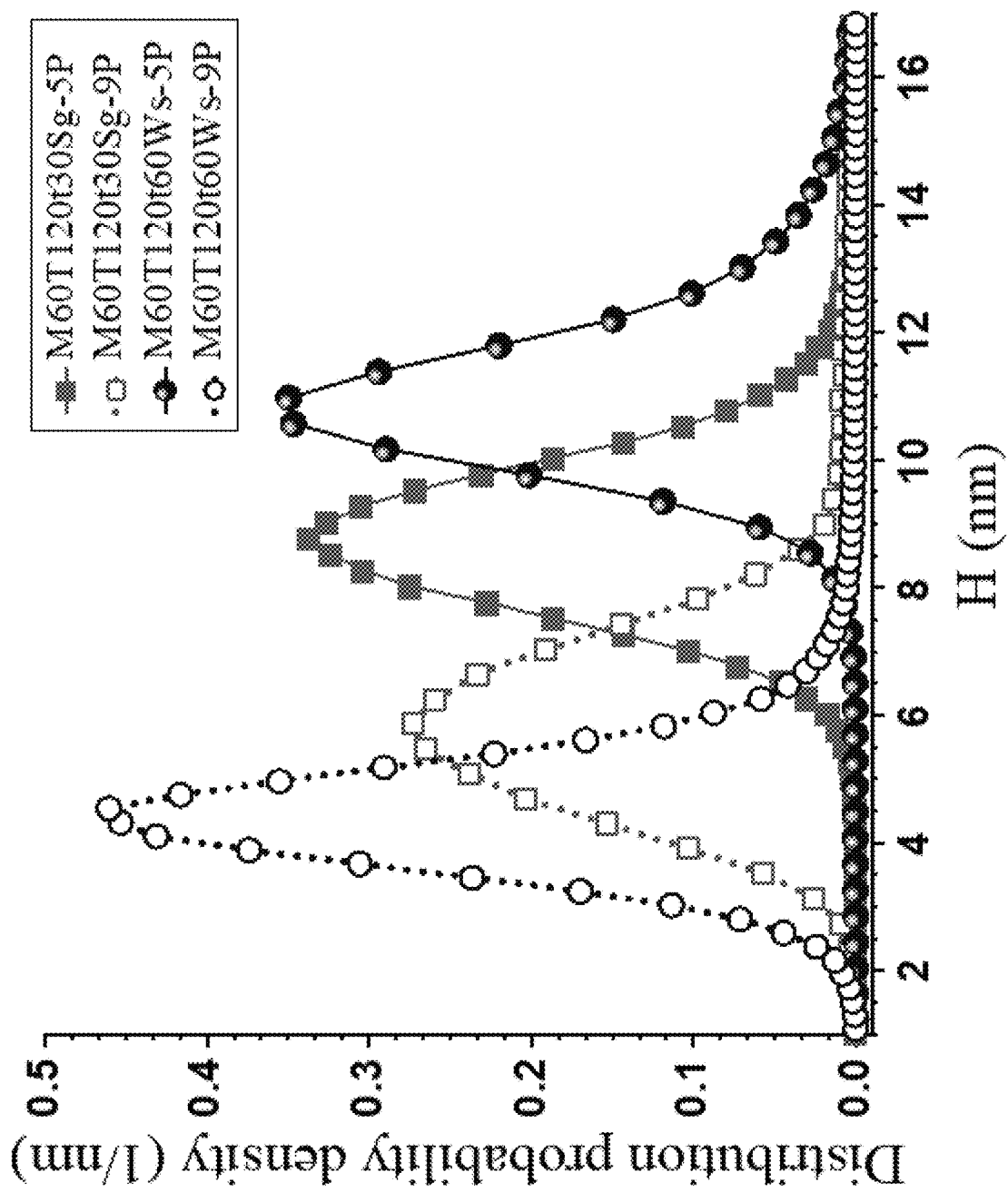
FIG. 17. Maleic acid hydrotropic fractionation conditions on resultant wheat straw and switchgrass LCNF fibril height distribution probability density from AFM topographical measurements.

Example 13: Producing Lignin-Containing Cellulose Nanofibrils from Maleic Acid Fractionated Wheat Straw and Switchgrass Cellulosic Solids The MA fractionated WISs from wheat straw and switchgrass were also evaluated for producing lignin containing cellulose nanofibrils (LCNFs). The results indicate that 5 passes through microfluidization is more than sufficient to fibrillate the WIS into nanoscale fibrils as revealed by AFM measurements shown in FIGS. 16A-16D. The AFM topographic measured fibril height distributions indicate that the fibrils have height or diameter less than 15 nm as shown in FIG. 17. Increasing the extent of fibrillation reduced fibril height. Similar to birch wood LCNFs, the LCNFs from wheat straw and switchgrass were all carboxylated as listed in Table 12 and with good surface charge.

TABLE 12

List of water retention value, carboxyl group content, and surface charge of LCNF (5 and 9 passes through the 200 and 87 μm chamber in the microfluidizer).

| Samples | Water retention value (%) | Carboxyl group content (mmol/g) | Surface charge (mV) |
|---|---|---|---|
| M60T120t60-5WS | 758 | 0.141 ± 0.009 | −40.70 ± 2.2 |
| M60T120t60-9WS | 849 | 0.144 ± 0.08 | −43.84 ± 3.4 |
| M60T120t30-5SG | 706 | 0.198 ± 0.008 | −34.79 ± 2.9 |
| M60T120t30-9SG | 848 | 0.226 ± 0.010 | −37.31 ± 2.4 |

Example 14: Reducing Lignin Condensation to Facilitate Pulp Bleaching

Figure 18:
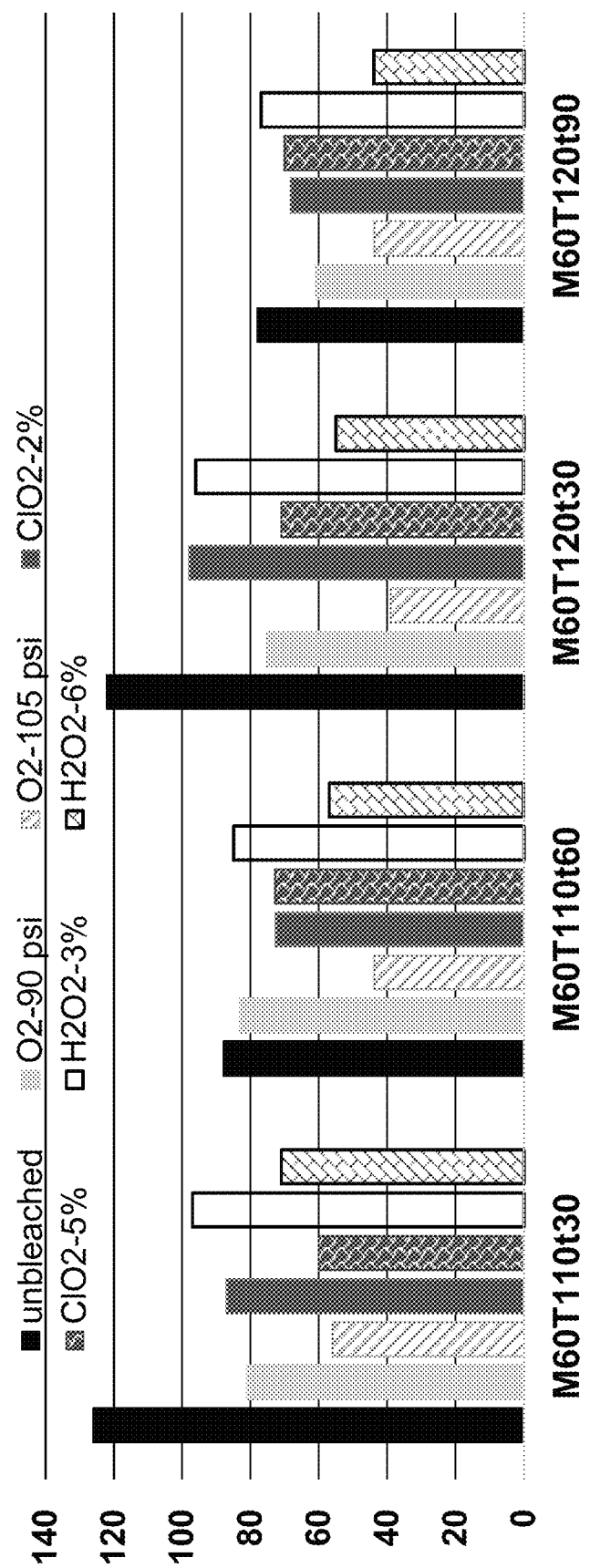
FIG. 18. Single stage bleaching using different chemicals on wheat straw fibers from different fractionation conditions: fiber kappa number (a measure of lignin content).

Earlier studies indicated that less condensation of lignin in pulp fibers with high β-O-4 linkages can improve pulp bleaching (Froass et al., 1996; Gellerstedt & Al-Dajani, 2000). However, available strategies to reduce lignin condensation were not effective because industrial alkaline pulping requires delignification at high temperatures of approximately 150° C. or higher for approximately 2 hours. Low temperature acid hydrotropic fractionation with rapid delignification provided the opportunity to reduce lignin condensation to facilitate bleaching with reduced bleaching chemical loadings, as recently demonstrated (Ma et al., 2020). To evaluate the effect of lignin condensation on bleaching, four WISs from wheat straw fractionated by MA under the conditions M60T110t30, M60T110t60, M60T120t30, and M60T120t90 were bleached using different chemistries, i.e., chlorine dioxide, hydrogen peroxide, oxygen, and a combination of these chemicals. The kappa number, a measure of lignin content used in the pulp and paper industry, of the unbleached and bleached WISs is shown in FIG. 18. Comparing the two pairs of WISs fractionated at 110° C. (M60T110t30 and M60T120t60) and 120° C. (M60T120t30 and M60T120t90), a shorter fractionation time of 30 min in each pair represents a lower severity than the run with a longer fractionation time of either 60 min or 90 min; in other words, the fractionation of 30 min resulted in a lower degree of lignin condensation than the run with a longer time. However, the bleached sample kappa numbers from each of the lower severity fractionation runs, using the various bleaching chemistries, were not significantly higher, or in some cases were even lower, than the corresponding bleached samples from the corresponding higher severity fractionations. This is in spite of the fact that the unbleached kappa numbers of the higher severity runs (kappa approximately 80 and lignin content 14%) were significantly lower than the kappa number of the lower severity run (over 120, or lignin content 17%). This suggests that the lower severity run with low lignin condensation can facilitate bleaching. Oxygen delignification at oxygen pressure 115 psi alone can reduce the WIS kappa number by as much as two thirds for the lower severity run at 120° C. The bleachability of a WIS is most hindered by lignin condensation when using chlorine dioxide. Even at a higher chlorine dioxide dosage of 5%, kappa reduction was minimal for WIS from the two higher severity runs, M60T110t60 and M60T120t90. A similar phenomenon was also observed from the two higher severity runs using hydrogen peroxide at a low dosage of 3%.

Figure 19:
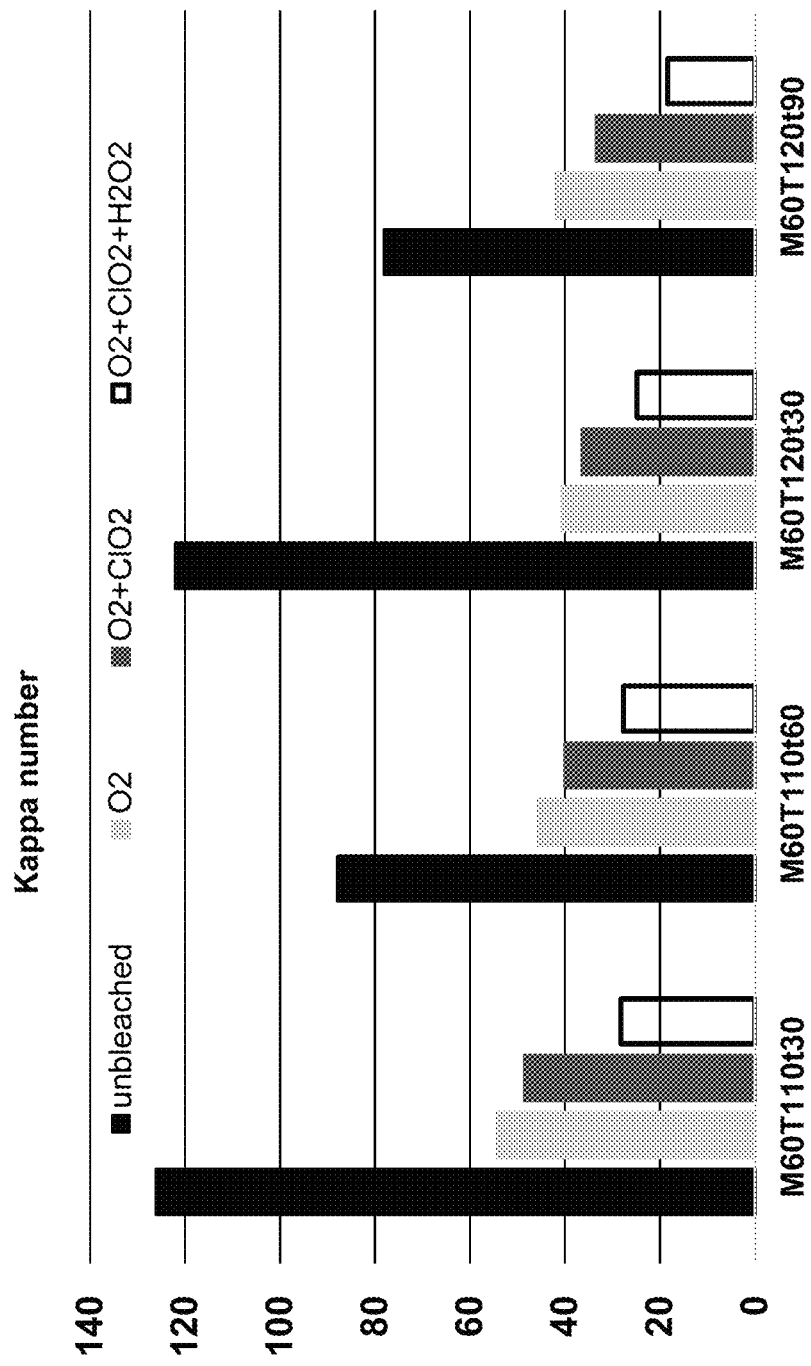
FIG. 19. Comparisons of different bleaching sequences on the kappa number of wheat straw fibers from different fractionation conditions.
Figure 20:
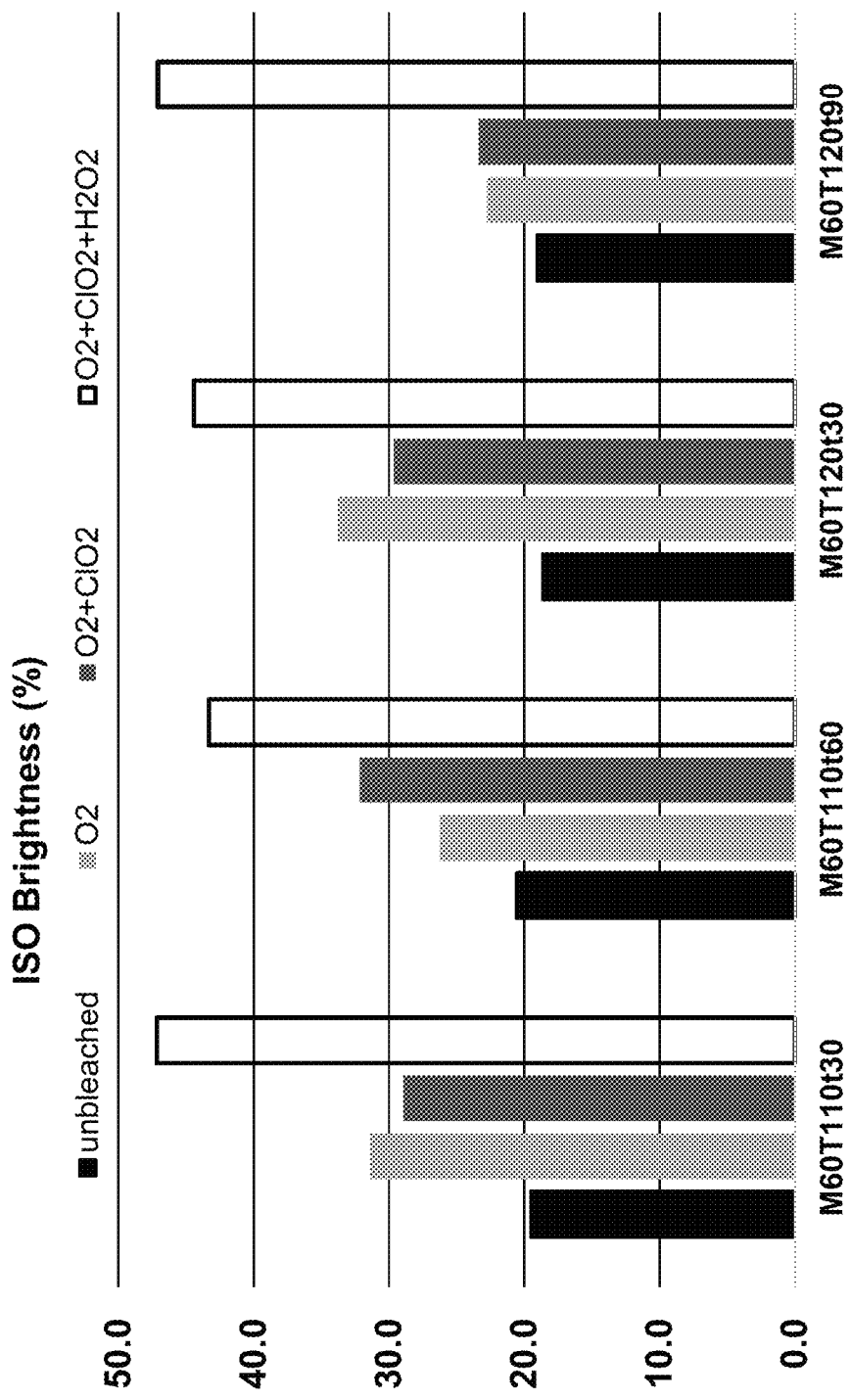
FIG. 20. Comparisons of different bleaching sequences on the brightness of wheat straw fibers from different fractionation conditions.

Following a traditional industry bleaching practice, a bleaching sequence was designed using oxygen at 110° C. followed by $ClO_2$ at a charge of 5% and then hydrogen peroxide at a charge of 6%. This sequence was applied to the four WISs discussed above. The kappa number can be reduced from over 120 to approximately 25 for all the WISs, as shown in FIG. 19. Fiber brightness was increased from 20 ISO% to approximately 45 ISO%, as shown in FIG. 20. It appears that there are no advantages in using high severity fractionation. The results also suggest that $ClO_2$, a traditional bleaching chemical widely used in the pulp and paper industry, has limited effect in decreasing fiber kappa number and increasing fiber brightness. Photos of the handsheets made from bleached WISs showed that the differences in the appearance among these four bleached WISs fractionated under very different severities were not significant. The key feature is the presence of bulk undelignified fibers that may significantly affect pulp brightness. This suggests more delignification than the samples discussed here of approximately 70% (the two high severity runs) is needed to remove bulk lignin to obtain high fiber brightness. The next example is trying to address this issue, especially under lower acid concentrations.

Example 15: Spiking Strong Acid in MA Fractionation to Improve Delignification

MA is weak acid. To promote acidolysis to facilitate delignification, a small amount of sulfuric acid was spiked in MA fractionation of hammer milled birch wood under 3 fractionation conditions. As listed in Table 13, spiking a very small amount of sulfuric acid at 1% resulted in substantial improvement in lignin dissolution for MA fractionation at low severities. For example, under M50T110t30, spiking sulfuric acid to 1 wt. % concentration in the acid solution increased delignification from 32.8% to 45.1%, or by 37.5%, based on measured lignin content in water washed WISs. The increment was reduced under M60T110t30, i.e., from 53.3% to 60.5%, or by only 13.5%. Furthermore, increasing sulfuric acid loading had a diminishing effect, i.e., delignification was increased to only 63.5% from 60.5% when sulfuric acid loading was increased from 1 wt. % to 3 wt. %. Under M70T110t30, water washing was not enough to remove re-precipitated dissolved lignin due to lignin condensation, resulting in reduced lignin removal from WIS. Acetone washing, which suggested spiking sulfuric acid, did not improve delignification under high severity M70T110t30. Spiking sulfuric acid also improved xylan dissolution; however, it did not increase cellulose degradation, as listed in Table 13.

TABLE 13

Effect of spiking sulfuric acid in MA fractionation of birch wood on chemical composition and component retained (the numbers in the parentheses).

| WIS Sample | Glucan (%) | Xylan (%) | Klason Lignin (%) | WIS yield (%) |
|---|---|---|---|---|
| Birch wood Water Washed | 40.0 | 23.0 | 19.5 | 100 |
| M50T110t30 | 52.2 (85.4) | 12.5 (35.6) | 20.0 (67.2) | 65.4 |
| M50T110t30 + 1 wt. % $H_2SO_4$ | 57.6 (87.0) | 11.5 (30.2) | 17.8 (54.9) | 60.3 |
| M60T110t30 | 60.7 (86.6) | 11.8 (29.3) | 16.0 (46.7) | 57.0 |
| M60T110t30 + 1 wt. % $H_2SO_4$ | 62.5 (86.7) | 11.7 (28.2) | 13.9 (39.5) | 55.4 |
| M60T110t30 + 3 wt. % $H_2SO_4$ | 64.0 (86.7) | 8.5 (20.1) | 13.1 (36.5) | 54.2 |
| M70T110t30 | 61.0 (85.8) | 11.5 (28.2) | 12.1 (35.0) | 56.2 |
| M70T110t30 + 1 wt. % $H_2SO_4$ | 62.8 (94.8) | 10.5 (27.6) | 15.4 (47.7) | 60.3 |
| Acetone Washed [a] | | | | |
| M50T110t30 | 55.0 (84.1) | 12.6 (33.4) | 15.9 (49.9) | 61.2 |
| M50T110t30 + 1 wt. % $H_2SO_4$ | 60.5 (85.6) | 11.6 (28.5) | 13.6 (39.5) | 56.5 |
| M60T110t30 | 62.5 (83.4) | 13.2 (30.7) | 12.5 (34.1) | 53.3 |
| M60T110t30 + 1 wt. % $H_2SO_4$ | 65.7 (84.4) | 11.7 (26.2) | 10.6 (27.9) | 51.3 |
| M60T110t30 + 3 wt. % $H_2SO_4$ | 67.2 (83.3) | 10.4 (22.3) | 8.1 (20.5) | 49.6 |
| M70T110t30 | 64.8 (84.4) | 11.8 (26.7) | 8.0 (21.3) | 52.0 |
| M70T110t30 + 1 wt. % $H_2SO_4$ | 69.4 (94.5) | 11.5 (27.1) | 7.8 (21.8) | 54.4 |

[a] Samples washed with acetone solution, acetone:water (v:v) = 9:1, at room temperature under WIS:acetone solution ratio approximately 1:10 for 3 times. Washing was conducted in a shaker at 200 rpm for 5 min.

REFERENCES

Bian, H., Chen, L., Dai, H., Zhu, J.Y. 2017a. Integrated production of lignin containing cellulose nanocrystals (LCNC) and nanofibrils (LCNF) using an easily recyclable di-carboxylic acid. *Carbohydrate Polymers*, 167, 167-176.

Bian, H., Chen, L., Gleisner, R., Dai, H., Zhu, J.Y. 2017b. Producing wood-based nanomaterials by rapid fractionation of wood at 80° C. using a recyclable acid hydrotrope. *Green Chem.*, 19, 3370-3379.

Bian, H., Chen, L., Dai, H., Zhu, J.Y. 2017c. Effect of fiber drying on properties of lignin containing cellulose nanocrystals and nanofibrils produced through maleic acid hydrolysis. *Cellulose*, 24(10), 4205-4216.

Cai, C., Hirth, K., Gleisner, R., Lou, H., Qiu, X., Zhu, J.Y. 2020. Maleic acid as a dicarboxylic acid hydrotrope for sustainable fractionation of wood at atmospheric pressure and ≤100° C.: Mode and utility of lignin esterification. *Green Chem.*, 22(5), 1605-1617 DOI: 10.1039/C9GC04267A.

Chen, L., Zhu, J.Y., Baez, C., Kitin, P., Elder, T. 2016. Highly thermal-stable and functional cellulose nanocrystals and nanofibrils produced using fully recyclable organic acids *Green Chem.*, 18, 3835-3843.

Cheng, J., Hirth, K., Ma, Q., Zhu, J., Wang, Z., Zhu, J.Y. 2019. Toward sustainable and complete wood valorization by fractionating lignin with low condensation using an acid hydrotrope at low temperatures (≤80° C.). *Ind. Eng. Chem. Res.*, 58, 7063-7073 DOI: 10.1021/acs.iecr.9b00931.

Davis, M.W. 1998. A rapid modified method for compositional carbohydrate analysis of lignocellulosics by high pH anion-exchange chromatography with pulsed amperometric detection (HPAEC/PAD). *Journal of Wood Chemistry and Technology*, 18(2), 235-352.

Deuss, P.J., Lancefield, C.S., Narani, A., De Vries, J.G., Westwood, Nj., Barta, K. 2017. Phenolic acetals from lignins of varying compositions: Via iron(iii) triflate catalysed depolymerisation. *Green Chemistry*, 19(12), 2774-2782.

Ewanick, S.M., Bura, R., Saddler, J.N. 2007. Acid-catalyzed steam pretreatment of lodgepole pine and subsequent enzymatic hydrolysis and fermentation to ethanol. *Biotechnology and Bioengineering*, 98(1), 737-746.

Friberg, S.E., Rananavare, S.B., Osborne, D.W. 1986. The mechanism of hydrotrope action of a dicarboxylic acid. *Journal of Colloid And Interface Science*, 109(2), 487-492.

Froass, P.M., Ragauskas, A.J., Jiang, J.E. 1996. Chemical structure of residual lignin from kraft pulp. *Journal of Wood Chemistry and Technology*, 16(4), 347-365.

Gellerstedt, G., Al-Dajani, W.W. 2000. Bleachability of alkaline pulps. Part 1. The importance of β-aryl ether linkages in lignin. *Holzforschung*, 54(6), 609-617.

Gellerstedt, G., Lindfors, E.L. 1984. Structural changes in lignin during kraft pulping. *Holzforschung*, 38(3), 151-158.

Gu, F., Gilles, W., Gleisner, R., Zhu, J.Y. 2016. Fermentative high titer ethanol production from a Douglas-fir forest residue without detoxification using SPORL: High SO2 loading at a low temperature. *Ind. Biotechnol.*, 12(3), 168-175.

Iakovlev, M., van Heiningen, A. 2012. Efficient fractionation of spruce by SO2-ethanol-water treatment: Closed mass balances for carbohydrates and sulfur. *ChemSusChem*, 5(8), 1625-1637.

Kringstad, K.P., Mörck, R. 1983. $^{13}$CNMR Spectra of Kraft Lignins. *Holzforschung*, 37(5), 237-244.

Luo, X., Gleisner, R., Tian, S., Negron, J., Horn, E., Pan, X.J., Zhu, J.Y. 2010. Evaluation of mountain beetle infested lodgepole pine for cellulosic ethanol production by SPORL pretreatment. *Ind. Eng. Chem. Res.*, 49(17), 8258-8266.

Ma, Q., Hirth, K., Zhai, H., Zhu, J.Y. 2020. Highly bleachable wood fibers containing less condensed lignin from acid hydrotropic fractionation (AHF). *ACS Sustainable Chem. Eng.*, 8, 9046-9057 DOI: 10.1021/acssuschemeng.0c02129.

Mino, J., Matijević, E., Meites, L. 1977. Long-chain dicarboxylic acids. I. Characterization of 5-(and 6-)carboxy-4-hexyl-2-cyclohexen-1-yl octanoic acid solutions. *Journal of Colloid And Interface Science*, 60(1), 148-153.

Moon, R.J., Martini, A., Nairn, J., Simonsen, J., Youngblood, J. 2011. Cellulose nanomaterials review: structure, properties and nanocomposites. *Chem. Soc. Rev.*, 40, 3941-3994.

Nelson, K., Retsina, T., Pylkkanen, V., O'Connor, R. 2015. Processes and apparatus for producing nanocellulose, and compositions and products produced therefrom. U.S. Pat. No. 9,187,865 B2.

Pan, X., Gilkes, N., Kadla, J., Pye, K., Saka, S., Gregg, D., Ehara, K., Xie, D., Lam, D., Saddler, J. 2006. Bioconversion of hybrid poplar to ethanol and co-products using an organosolv fractionation process: Optimization of process yields. *Biotechnology and Bioengineering*, 94(5), 851-861.

Renders, T., Van den Bosch, S., Koelewijn, S.-F., Schutyser, W., Sels, B. 2017. Lignin-first biomass fractionation: the advent of active stabilisation strategies. *Energy & Environmental Science*, 10(7), 1551-1557.

Rinaldi, R., Jastrzebski, R., Clough, M.T., Ralph, J., Kennema, M., Bruijnincx, P.C.A., Weckhuysen, B.M. 2016. Paving the Way for Lignin Valorisation: Recent Advances in Bioengineering, Biorefining and Catalysis. *Angewandte Chemie-International Edition*, 55(29), 8164-8215.

Rojo, E., Peresin, M.S., Sampson, W.W., Hoeger, I.C., Vartiainen, J., Laine, J., Rojas, O.J. 2015. Comprehensive elucidation of the effect of residual lignin on the physical, barrier, mechanical, and surface properties of nanocellulose films. *Green Chem.*, 17, 1853-1866.

Shuai, L., Amiri, M.T., Questell-Santiago, Y.M., Héroguel, F., Li, Y., Kim, H., Meilan, R., Chapple, C., Ralph, J., Luterbacher, J.S. 2016. Formaldehyde stabilization facilitates lignin monomer production during biomass depolymerization. *Science*, 354(6310), 329-333.

Spence, K.L., Venditti, R.A., Habibi, Y., Rojas, O.J., Pawlak, J.J. 2010. The effect of chemical composition on microfibrillar cellulose films from wood pulps: Mechanical processing and physical properties. *Bioresource Technology*, 101(15), 5961-5968.

Sun, Z., Fridrich, B., De Santi, A., Elangovan, S., Barta, K. 2018. Bright Side of Lignin Depolymerization: Toward New Platform Chemicals. *Chemical Reviews*, 118(2), 614-678.

Ward, B.F., Force, C.G., Bills, A.M., Woodward, F.E. 1975. Industrial utilization of $C_{21}$ dicarboxylic acid. *Journal of the American Oil Chemists Society*, 52(7), 219-224.

Zhu, H., Luo, W., Ciesielski, P.N., Fang, Z., Zhu, J.Y., Henriksson, G., Himmel, M.E., Hu, L. 2016. Wood-derived materials for green electronics, biological devices, and energy applications. *Chem. Rev.*, 116(16), 9305-9374.

Zhu, J.Y., Pan, X.J., Wang, G.S., Gleisner, R. 2009. Sulfite pretreatment (SPORL) for robust enzymatic saccharification of spruce and red pine. *Bioresour. Technol.*, 100(8), 2411-2418.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method for fractionating lignocellulosic biomass, the method comprising:
   dispersing a lignocellulosic biomass in an aqueous solution comprising maleic acid, wherein the lignocellulosic biomass has not undergone a pulping that reduces its lignin content and further wherein the concentration of the maleic acid in the solution is higher than its minimal hydrotrope concentration;
   reacting the lignocellulosic biomass with the maleic acid at a temperature and for a time sufficient to carboxylate the lignin and to dissolve at least 10 wt. % of the lignin in the lignocellulosic biomass; and
   separating the solution and the dispersed lignocellulosic biomass into a spent acid solution comprising dissolved carboxylated lignin and a water-insoluble cellulose-rich solids fraction comprising water-insoluble lignocellulosic solid residues.

2. The method of claim 1, wherein the dissolved lignin has a degree of condensation of 20% or lower.

3. The method of claim 1, wherein the temperature is no greater than 120° C. and the time is no greater than 120 minutes.

4. The method of claim 3, wherein the temperature is in the range from 70° C. to 120° C., the time is in the range from 10 minutes to 60 minutes, and the concentration of maleic acid in the solution is in the range from 25 wt. % to 85 wt. %.

5. The method of claim 1, wherein the lignocellulosic biomass comprises wood chips, milled wood, or a combination thereof.

6. The method of claim 1, wherein the lignocellulosic biomass is a hardwood and from 20 wt. % to 65 wt. % of the lignin in the lignocellulosic biomass is dissolved by the maleic acid.

7. The method of claim 6, wherein the temperature is in the range from 80° C. to 110° C., the time is in the range from 10 minutes to 30 minutes, and the concentration of maleic acid in the solution is in the range from 40 wt. % to 85 wt. %.

8. The method of claim 6, wherein the temperature is in the range from 70° C. to 120° C., the time is in the range from 30 minutes to 60 minutes, and the concentration of maleic acid in the solution is in the range from 25 wt. % to 40 wt. %.

9. The method of claim 1, further comprising fibrillating the lignocellulosic biomass prior to dispersing the lignocellulosic biomass in the aqueous solution comprising the maleic acid.

10. The method of claim 1, further comprising precipitating lignin nanoparticles from the spent acid solution.

11. The method of claim 1, further comprising converting sugars dissolved in the spent acid solution into furans and separating the furans from the spent acid solution.

12. The method of claim 1, further comprising mechanically fibrillating the lignocellulosic solid residues to form lignocellulosic microfibrils, lignocellulosic nanofibrils, or a combination thereof.

13. The method of claim 12, wherein the lignocellulosic microfibrils, lignocellulosic nanofibrils, or the combination thereof have a carboxyl group concentration in the range from 0.1 to 0.4 mmol/g.

14. The method of claim 1, further comprising converting the water-insoluble lignocellulosic solid residues into sugars via hydrolysis by enzymes or chemicals.

15. The method of claim 1, further comprising recycling the maleic acid in the spent acid solution back into the aqueous solution comprising the dispersed lignocellulosic biomass.

16. The method of claim 1, wherein the lignocellulosic biomass is non-woody biomass.

17. The method of claim 16, wherein the lignocellulosic biomass is wheat straw.

18. The method of claim 16, wherein the lignocellulosic biomass is switchgrass.

19. The method of claim 1, wherein the lignocellulosic biomass is raw wood.

20. The method of claim 19, wherein the raw wood in in the form of wood chips.

* * * * *